United States Patent

Krutak et al.

Patent Number: 5,525,516
Date of Patent: Jun. 11, 1996

[54] METHOD FOR TAGGING PETROLEUM PRODUCTS

[75] Inventors: James J. Krutak; Michael R. Cushman; Max A. Weaver, all of Kingsport, Tenn.

[73] Assignee: Eastman Chemical Company, Kingsport, Tenn.

[21] Appl. No.: 315,386

[22] Filed: Sep. 30, 1994

[51] Int. Cl.$^6$ .................................................. G01N 21/64
[52] U.S. Cl. .................. 436/56; 436/27; 436/29; 436/172
[58] Field of Search ................. 436/27, 29, 56, 436/172

[56] References Cited

U.S. PATENT DOCUMENTS

| | | | |
|---|---|---|---|
| 2,058,774 | 10/1936 | Colligan | 87/9 |
| 2,925,333 | 2/1960 | Thompson et al. | 44/59 |
| 3,004,821 | 1/1961 | Gano | 8/3 |
| 3,164,449 | 1/1965 | Buxbaum | 44/59 |
| 3,350,384 | 10/1967 | Conway | 260/184 |
| 3,435,054 | 3/1969 | Kranz et al. | 260/378 |
| 3,574,550 | 4/1971 | Scott | 23/230 |
| 3,630,941 | 12/1971 | Bergmark | 252/186 |
| 3,690,809 | 9/1972 | Orelup | 8/6 |
| 3,704,106 | 11/1972 | Orelup | 44/59 |
| 3,862,120 | 1/1975 | Orelup | 260/191 |
| 4,009,008 | 2/1977 | Orelup | 44/59 |
| 4,049,393 | 9/1977 | Orelup | 44/59 |
| 4,209,302 | 6/1980 | Orelup | 436/56 |
| 4,278,444 | 7/1981 | Beyer et al. | 44/59 |
| 4,303,407 | 12/1981 | Marangelli et al. | 8/643 |
| 4,540,595 | 9/1985 | Acitelli et al. | 427/7 |
| 4,659,676 | 4/1987 | Rhyne | 436/56 |
| 4,735,631 | 4/1988 | Orelup | 44/59 |
| 4,755,469 | 7/1988 | Shewalter | 436/27 |
| 4,764,474 | 9/1988 | Orelup | 436/111 |
| 4,992,204 | 2/1991 | Kluger | 252/301.16 |
| 5,093,147 | 3/1992 | Andrus et al. | 427/7 |
| 5,143,853 | 9/1992 | Walt | 436/501 |
| 5,201,921 | 4/1993 | Luttermann et al. | 8/506 |
| 5,279,967 | 1/1994 | Bode | 436/56 |
| 5,292,855 | 3/1994 | Krutak | 191/64 |
| 5,336,714 | 8/1994 | Krutak | 524/608 |

FOREIGN PATENT DOCUMENTS

| | | |
|---|---|---|
| 95975 | 7/1983 | European Pat. Off. . |
| 1913912 | 10/1970 | Germany . |
| 297659 | 11/1971 | U.S.S.R. . |
| WO93/09172 | 5/1994 | WIPO . |

OTHER PUBLICATIONS

PCT International Publication No. WO94/12874, 9 Jun. 1994.

Primary Examiner—Jill Warden
Assistant Examiner—Sharidan Carrillo
Attorney, Agent, or Firm—Karen A. Harding; Harry J. Gwinnell

[57] ABSTRACT

This invention provides a method for imparting invisible markings for identification purposes to petroleum hydrocarbons by incorporating one or more infrared fluorescing compounds therein. Certain infrared fluorophores from the classes of squaraines (derived from squaric acid), phthalocyanines and naphthalocyanines are useful in providing invisibly marked petroleum hydrocarbons such as crude oil, lubricating oils, waxes, gas oil (furnace oil), diesel oil, kerosene and in particular gasoline. The near infrared fluorophores are added to the hydrocarbons at extremely low levels and are detected by exposing the marked hydrocarbon compositions to near infrared radiation having a wavelength in the 670–850 nm range and then detecting the emitted fluorescent light via near infrared light detection means.

32 Claims, 2 Drawing Sheets

METHOD FOR TAGGING PETROLEUM PRODUCTS

FIELD OF THE INVENTION

This invention belongs to the field of organic chemistry. In particular, this invention relates to a method for invisibly marking or tagging petroleum products for identification purposes.

BACKGROUND OF THE INVENTION

It is known that the various petroleum hydrocarbons can be marked using colorants. However, there exists a need for invisibly marking petroleum-derived products in order to identify the various grades of fuels, to distinguish manufacturer's brands, and to make misuse impossible or at least traceable. In this regard, it is desirable that the added marker be readily detected by non-scientific personnel. Finally, the marker should be detectable at low enough levels so that the physical and chemical properties of the petroleum product are not appreciably altered. Historically, various problems have accompanied the use of dyes or colorants as markers for petroleum products, including sludging, crystallization, or agglomeration of the dye upon standing or storage.

U.S. Pat. Nos. 2,028,637; 2,925,333; 3,004,821; 3,164,449; 3,350,384; 3,435,054; 3,690,809; 3,704,106; 4,009,008; 4,049,393; 4,303,407; and 4,735,631; European Application No. 95 975; and U.S.S.R. Patent No. 297,659 describe the use of colorants and dyes in marking petroleum products.

Ger. Offen. 1,913,912; and U.S. Pat. Nos. 4,278,444, 4,992,204; and 5,279,967 describe visible or ultraviolet fluorescing compounds useful as markers in petroleum products. The marking or tagging systems based on UV fluorescence have the inherent disadvantage that many of the petroleum hydrocarbons themselves contain condensed aromatic compounds which fluoresce when exposed to UV radiation.

U.S. Pat. No. 5,201,921 describes a method for marking plastic with UV fluorescent compounds.

U.S. Pat. No. 4,540,595 teaches the marking of documents such as bank checks with certain fluorescent phenoxazine dyes.

U.S. Pat. No. 5,093,147 describes the use of polymethine infrared fluorescent compounds in bar codes.

U.S. Pat. No. 3,630,941 describes 16,17-dialkoxy-violanthrones vat dyes for use as infrared fluorescers for marking articles.

All of the above infrared fluorophores lack adequate solubility in most petroleum hydrocarbons to be suitable for such use.

This invention provides a method for marking or tagging various petroleum products, for identification purposes. Preferably, the markers of the present invention are squaraines, phthalocyanines, or naphthalocyanines which fluoresce in the near infrared region when exposed to near infrared light. Also provided are certain near infrared fluorophoric compounds which are soluble in petroleum hydrocarbons.

BRIEF DESCRIPTION OF THE DRAWINGS

FIGS. 1 and 2 are more fully described below.

SUMMARY OF THE INVENTION

Figure 1:
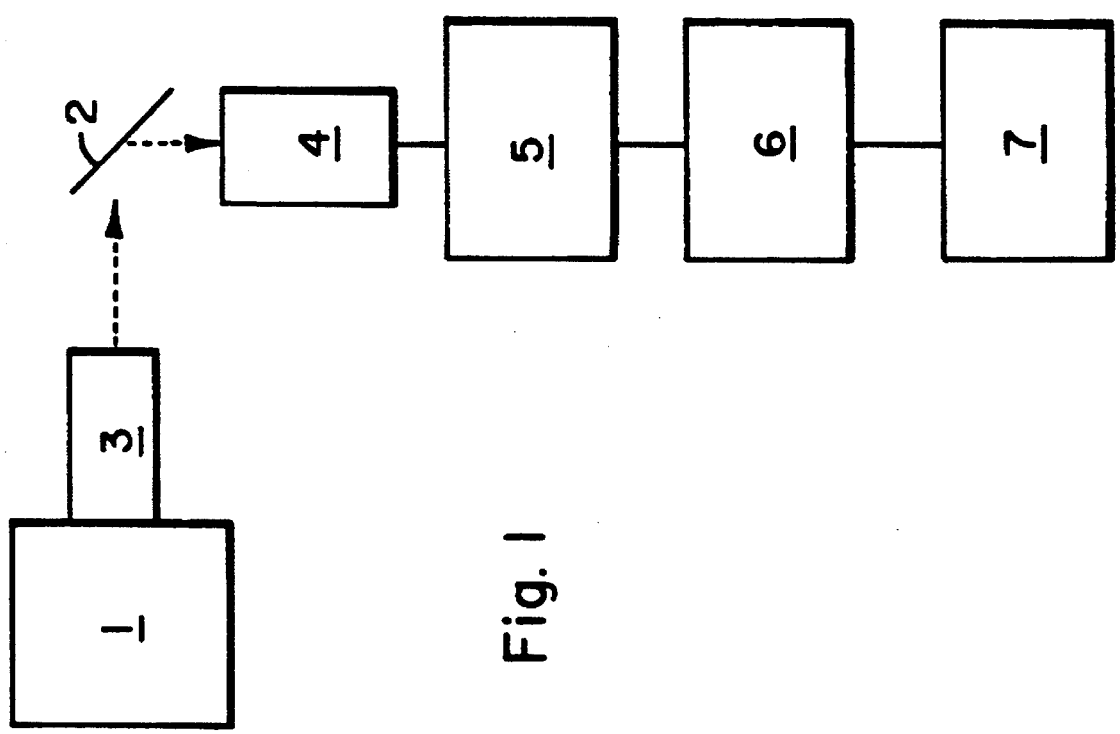
FIG. 1 depicts an apparatus useful for practicing the present invention for identification of the near infrared (NIR) marker in the petroleum products as described herein. This arrangement will be understood to be an application of commercially available fluorometers. As may be seen from FIG. 1, there is present a light source (1) capable of emitting radiation in the visible and NIR region which illuminates the near infrared fluorophore-marked sample (2) through a wavelength selector (3) e.g., monochromator or interference filter. A wavelength selector (4) and a NIR sensitive photodetector (5) is placed at 90° or less angle. It may be seen from FIG. 1 that light source (1), wavelength selector (3 & 4) and photodetector (5) are all arranged on two sides of a triangle to minimize scattered light entering the detector. The light source (1) in FIG. 1 may be replaced with lasers, preferably semiconductor lasers. The output of photodetector (5) is provided to level adjustment amplifier (6), the output of which is provided to an integrated circuit digital multimeter (7). The output of the digital multimeter is connected to a computer display so as to provide a numeral and graphical indication of the amount of luminous flux at the predetermined wavelength (preferably at the emission maxima) emitted by the substance contained in sample.
Figure 2:
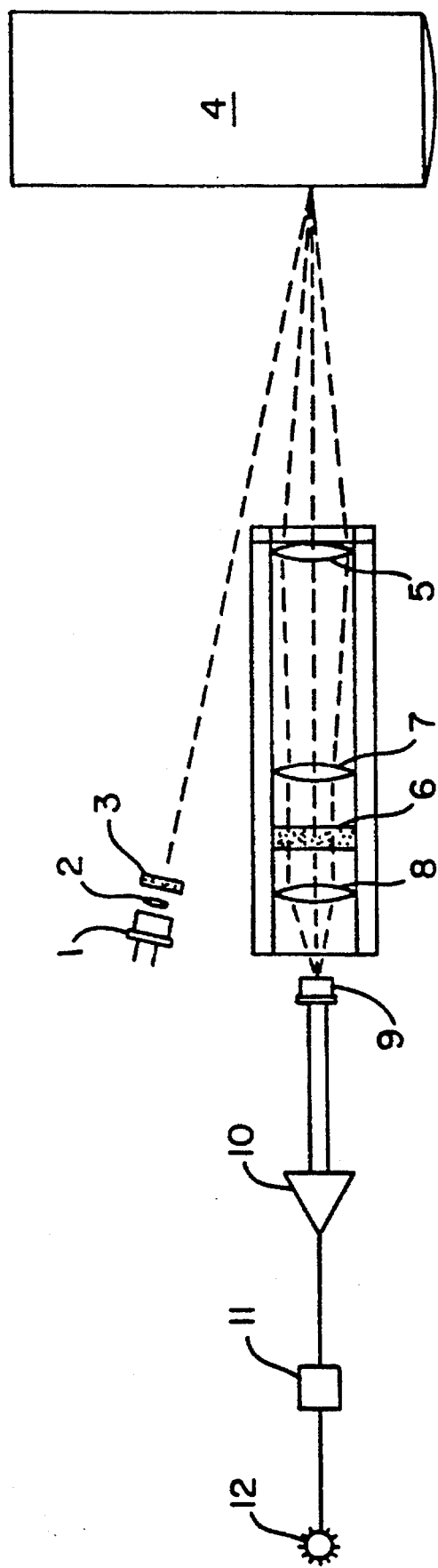
FIG. 2 shows a preferred apparatus useful for practice of the present invention which will be understood to be a specialized arrangement for performing the tests of the present invention. As may be seen from FIG. 2, there is present a laser diode light source (1) capable of emitting radiation in the NIR region which is collimated through a collimating lens (2), and illuminates the sample (4) through an optical filter (3). A focusing lens (5) and a beam compressor are placed at 30 degrees or less angle. It may be seen from FIG. 2 that the laser diode light source and the collimating lens are arranged to minimize scattered light from entering the detector. An optical filter (6) is placed between the compressor lenses (7 & 8) to select the wavelength of fluorescence of the tagging molecule which is focused on the photodetector. A current-to-voltage converter is connected to the photodetector (9) to amplify the detector signal. The arrangement and the electronic circuitry of the current-to-voltage amplifying (10) is widely known and the routines of amplifying and processing the photodetector signal are also well-known. The signal from the current-to-voltage converter circuit is detected by a threshold detector (11). The threshold level of the threshold detector is set at the level required to minimize any interference from unmarked samples. The presence of tagged samples in front of the preferred apparatus is indicated by the light-emitting diode (LED) indicator (12).

The present invention provides a method for tagging, for identification purposes, a petroleum product which comprises dissolving in said product a near infrared fluorophoric compound.

As a further aspect of the invention there is provided a petroleum product having dissolved therein at least one near infrared fluorophoric compound.

As a further aspect of the invention, there is provided a method for identifying a petroleum product, wherein said product has one or more near infrared fluorophoric compounds dissolved therein, which comprises the steps:
(a) exposure of a petroleum hydrocarbon composition to electromagnetic radiation having wavelengths of 670–850 nm, wherein said petroleum hydrocarbon composition comprises a petroleum hydrocarbon material having dissolved therein one or more near infrared fluorescent tagging compounds, wherein said tagging compound(s) is (are) present in a concentration sufficient to impart detectable fluorescence when exposed to electromagnetic radiation of about 670–850 nm provided by light sources; followed by (b) detection of the emitted fluorescent radiation by near infrared detection means.

DETAILED DESCRIPTION OF THE INVENTION

In the practice of the present invention, it is possible to mark, for example, one grade of gasoline with one near infrared flurophoric compound and another grade with a near infrared fluorophoric marker which fluoresces at a detectably different wavelength. In this fashion, the identity of a certain grade of gasoline can be confirmed without resorting to chemical analysis.

Ideally, the near infrared fluorophores useful in the practice of the invention should possess the following properties:
1. adequate solubility in petroleum hydrocarbons to allow easy dissolution to give concentrations of infrared fluorophore detectable by available infrared detectors;
2. strong absorbance of infrared light in the 670–850 nm wavelength range;
3. little or no absorbance in the 400 to about 670 nm range (visible), to permit essentially "invisible" markings;
4. strong infrared fluorescence when irradiated with infrared radiants having wavelengths of about 670–850 nm;
5. give detectable emission levels when added to petroleum hydrocarbons at extremely low levels, e.g. 1 ppm or less.
6. have adequate stability, e.g. to sunlight, water, oxygenates, temperature, etc.
7. be environmentally safe.

It is also within the scope of the invention to mark one or more petroleum hydrocarbons with two or more infrared fluorophores, said fluorescing compounds having been selected so that they absorb infrared and/or reemit fluorescent light at wavelengths different enough from each other as not to interfere with individual detection.

It is preferred that the infrared fluorophores absorb strongly at wavelengths below about 850 nm, since petroleum hydrocarbons have inherent interfering absorption of wavelengths above about 850 nm.

Growing concern about pollution from the use of petroleum fuels requires that any marker for petroleum hydrocarbons be added at the lowest levels possible to minimize any discharges into the atmosphere during combustion. Thus, the infrared fluorophore is preferably added at the lowest levels needed to produce a consistently detectable signal, preferably at about 1 ppm or less, by near infrared detection means, when irradiated by a light source.

The term "light sources" refers to devices used to irradiate the samples with near infrared radiation having wavelength outputs from 670 to 850 nm such as laser diodes, solid state lasers, dye lasers, incandescent, or any other known light source. Such light sources can be used in conjunction with wavelength selectors such as filters, monochromators, etc. The preferred light sources are those that have a maximum signal at the maximum of the absorbance of the tagging fluorophore. Examples include the laser diodes, light emitting diodes, or solid state lasers.

In the above method, it will be appreciated that near infrared detection means denotes any apparatus capable of detecting fluorescence in the range described herein. Such detection means are the devices for detecting photons emitted by the fluorescent samples at wavelengths of about 670 to 2500 nm such as photomultiplier tubes, solid state detectors, semi-conductor based detectors, or any such device. The preferred means of detection has an optimum sensitivity at the preferred wavelength region. Examples include the silicon photodiodes or germanium detectors.

In the above method, the phrase "detectibly different wavelength or wavelengths" refers to phenomenon that fluorescence by one or more of the near infrared fluorophores will occur at a different wavelength (or wavelengths in the case of two or more fluorophores) and such difference will, by necessity be one that is capable of detection. Using state of the art detection equipment it is believed that such differences in absorption/fluorescence of as little as 20 nm in wavelength can be discerned. Of course, this limitation is not critical and will decrease as detection methodology improves.

Thus, the presence of a near infrared fluorophore (NIRF) provides highly effective tags for identification of petroleum products. Ideally, as noted above, the NIRF "tag" should have good thermal stability and little light absorption in the visible region; that is they should impart little or no color to the petroleum product to which the NIRF is copolymerized or admixed with. Also, they should have strong absorption of near infrared light (high molar extinction coefficients, e.g., >20,000) and have strong fluorescence in the near infrared over the wavelengths of about 670–2500 nm. To produce essentially "invisible" tags the near infrared fluorescent compounds must absorb little if any light having wavelengths in the 400–670 nm range; however, since the compounds are present in extremely low concentrations, a small amount of absorption may be tolerated without imparting significant color.

The preferred near infrared fluorescent compounds which are useful in the practice of the invention are selected from the classes of phthalocyanines, 2,3-naphthalocyaninessquaraines (squaric acid derivatives) and croconic acid derivatives and correspond to Formulae I, II, III, and IV, respectively:

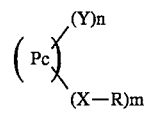

I

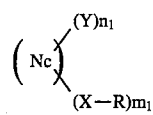

II

-continued

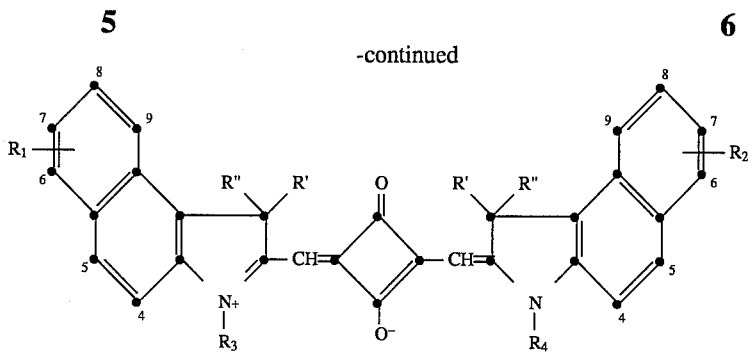

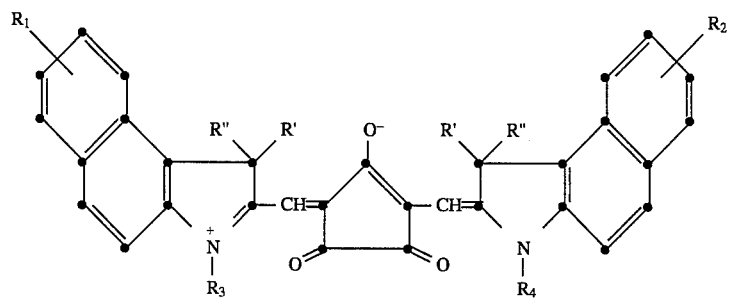

wherein Pc and Nc represent the phthalocyanine and naphthalocyanine moieties of Formulae Ia and IIa,

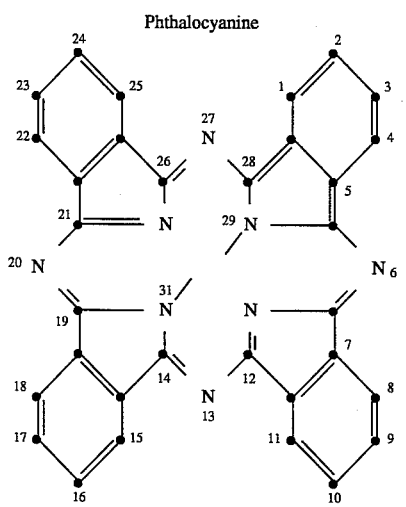

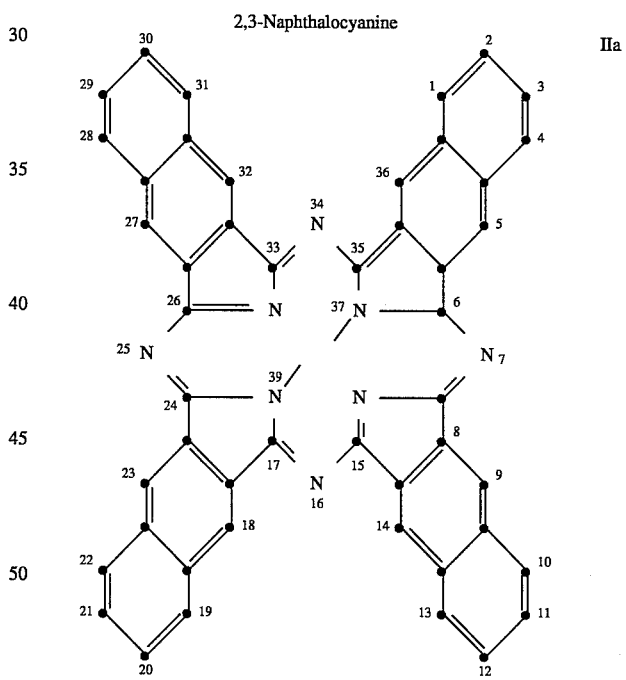

respectively, covalently bonded to hydrogen or to various halometals, organometallic groups, and oxymetals including AlCl, AlBr, AlF, AlOR$_5$, AlSR$_5$, SiCl$_2$, SiF$_2$, Si(OR$_6$)$_2$, Si(SR$_6$)$_2$, Zn or Mg, wherein R$_5$ and R$_6$ are selected from hydrogen, alkyl, aryl, heteroaryl, alkanoyl, arylcarbonyl, arylaminocarbonyl, trifluoroacetyl, $$-(CH_2CH_2O)_zR, \quad -(CH_2CHO)_zR$$
$$\qquad\qquad\qquad\qquad\quad |$$
$$\qquad\qquad\qquad\qquad\; CH_3$$

groups of the formula

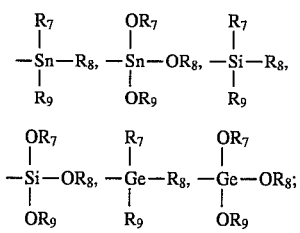

wherein $R_7$, $R_8$ and $R_9$ are independently selected from alkyl, phenyl or phenyl substituted with alkyl, alkoxy or halogen;

X is selected from oxygen, sulfur, selenium, tellurium or a group of the formula $N\text{-}R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, aryl, heteroaryl, halogen or hydrogen;

R is selected from hydrogen, unsubstituted or substituted alkyl, alkenyl, alkynyl, $C_3$–$C_8$ cycloalkyl, aryl, heteroaryl, alkylene

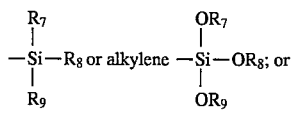

—$(X\text{-}R)_m$ is one or more groups selected from alkylsulfonylamino, arylsulfonylamino, or a group selected from the formulae —$X(C_2H_4O)_zR$,

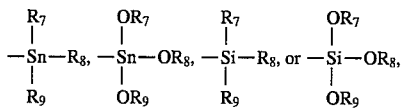

wherein R is as defined above; Z is an integer of from 1–4; or two —$(X\text{-}R)_m$ groups can be taken together to form divalent substituents of the formula

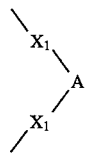

wherein each $X_1$ is independently selected from —O—, —S—, or —N–$R_{10}$ and A is selected from ethylene; propylene; trimethylene; and such groups substituted with lower alkyl, lower alkoxy, aryl and cycloalkyl; 1,2-phenylene and 1,2-phenylene containing 1–3 substituents selected from lower alkyl, lower alkoxy or halogen; R' and R" are independently selected from lower alkyl and cycloalkyl; $R_1$ and $R_2$ are independently selected from hydrogen, alkyl, alkoxy, halogen, aryloxy, alkylthio, arylthio, alkylsulfonyl, arylsulfonyl, alkylsulfonylamino, arylsulfonylamino, cycloalkylsulfonylamino, unsubstituted and substituted carbamoyl and sulfamoyl, alkoxycarbonyl, cycloalkoxycarbonyl, alkanoyloxy,

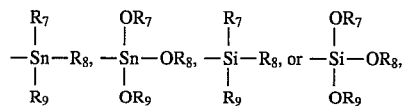

$R_3$ and $R_4$ are independently selected from hydrogen, lower alkyl, alkenyl or aryl; n is an integer from 0–16; $n_1$ is an integer from 0–24, m is an integer from 0–16; $m_1$ is an integer from 0–24; provided that the sums of n+m and $n_1+m_1$ are 16 and 24, respectively.

In the definitions of the substituents $(Y)n$, $(Y)n_1$, —$(XR)m$ and $(-X-R)m_1$ these substituents are not present when n, $n_1$, m and $m_1$ are zero, respectively. Substituents $(X-R)m$ and $(Y)n$ are present in compounds Ia on the peripheral carbon atoms, i.e. in positions 1, 2, 3, 4, 8, 9, 10, 11, 15, 16, 17, 18, 22, 23, 24, 25 and substituents $(X\text{-}R)m_1$ and $(Y)n_1$ are present on the peripheral carbon atoms of IIa, i.e. in positions 1, 2, 3, 4, 5, 9, 10, 11, 12, 13, 14, 18, 19, 20, 21, 22, 23, 27, 28, 29, 30, 31, 32 and 36.

In a preferred embodiment of this invention the near infrared fluorescing compound is a squaraine compound of Formula III, wherein $R_1$ and $R_2$ are independently alkoxycarbonyl.

In a further preferred embodiment of this invention, the near infrared fluorescing compound is a 2,3-naphthalocyanine compound of Formula II, wherein the naphthalocyanine moiety is bonded (at the 37 and 39 positions) to hydrogen, AlCl, AlOH, $AlOR_5$, $SiCl_2$, $Si(OH)_2$, $Si(OR_6)_2$, Zn or Mg, $m_1$ is 0, Y is selected from hydrogen and alkyl and $n_1$ is 24 with Y groups representing at least four alkyl or aryl groups.

In a further preferred embodiment of this invention, the near infrared fluorescing compound is a phthalocyanine compound of Formula I, wherein X is oxygen, R is aryl or alkyl, Y is hydrogen, m is 4, and n is 12; and wherein the phthalocyanine moiety is bonded (at the 29 and 31 positions) to hydrogen, AlCl, AlOH, $AlOCOCF_3$, $AlOR_5$, $SiCl_2$, $Si(OH)_2$, or $Si(OR_6)_2$, Zn or Mg.

In a further preferred embodiment, the phthalocyanine and naphthalocyanine compounds are bonded to hydrogen, i.e., at the 29 and 31 positions of the phthalocyanine and the 37 and 39 position of the naphthalocyanine.

In an especially preferred embodiment, the phthalocyanine, naphthalocyanine squaraine and croconic acid derivatives consist of carbon, hydrogen, and nitrogen atoms.

Other examples of preferred near infrared fluorescing compounds and moieties can be found in the tables below.

The term "lower alkyl" is used to represent straight or branched chain hydrocarbon radicals containing 1–6 carbons.

In the terms alkyl, alkoxy, alkylthio, alkylsulfonyl, alkoxycarbonyl, alkanoyl and alkanoyloxy, the alkyl portion of the groups contain 1–20 carbons and may contain straight or branched chains.

The term "cycloalkyl" is used to represent a cyclic aliphatic hydrocarbon radical containing 3–8 carbons, preferably 5 to 8 carbons and these radicals substituted by one or more groups selected from the group of alkyl, alkoxy or alkanoyloxy.

The alkyl and lower alkyl portions of the previously defined groups may contain as further substituents one or more groups selected from halogen, cyano, $C_1$–$C_6$-alkoxy, cycloalkyl, aryl, $C_1$–$C_6$-alkylthiol, arylthio, aryloxy, $C_1$–$C_6$-alkoxycarbonyl or $C_1$–$C_6$-alkanoyloxy.

The term "aryl" includes carbocyclic aromatic radicals containing 6–18 carbons, preferably phenyl and naphthyl, and such radicals substituted with one or more substituents selected from alkyl, alkoxy, halogen, —CH=N—alkyl, alkylthio, N(alkyl)₂, trifluromethyl, cycloalkyl, —CH=N—C₆H₄—CO₂ alkyl, alkoxycarbonyl, alkanoylamino, alkylsulfonylamino, arylsulfonylamino, cycloalkylsulfonylamino, alkanoyloxy, cyano, phenyl, phenylthio and phenoxy.

The term "heteroaryl" is used to represent mono or bicyclic hetero aromatic radicals containing at least one "hetero" atom selected from oxygen, sulfur and nitrogen or a combination of these atoms. Examples of suitable heteroaryl groups include: thiazolyl, benzothiazolyl, pyrazolyl, pyrrolyl, thienyl, furyl, thiadiazolyl, oxadiazolyl, benzoxazolyl, benzimidazolyl, pyridyl, pyrimidinyl and triazolyl. These heteroaryl radicals may contain the same substituents listed above as possible substituents for the aryl radicals. The term triazolyl also includes structure V and mixed isomers thereof,

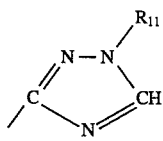

V wherein $R_{11}$ is hydrogen or selected from alkyl and alkyl substituted with one or two groups selected from halogen, alkoxy, aryl, cyano, cycloalkyl, alkanoyloxy or alkoxycarbonyl.

The terms "alkenyl and alkynyl" are used to denote aliphatic hydrocarbon moiety having 3–8 carbons and containing at least one carbon-carbon double bond and one carbon-carbon triple bond, respectively.

The term halogen is used to include bromine, chlorine, fluorine and iodine.

The term "substituted alkyl" is used to denote a straight or branched chain hydrocarbon radical containing 1–20 carbon atoms and containing as substituents 1 or 2 groups selected from halogen, cycloalkyl, cyano, $C_1$–$C_6$ alkoxy, aryl, $C_1$–$C_6$ alkylthio, arylthio, aryloxy, $C_1$–$C_6$ alkoxycarbonyl, or $C_1$–$C_6$ alkanoyloxy.

The term "substituted carbamoyl" is used to denote a radical having the formula —CONR₁₂R₁₃, wherein $R_{12}$ and $R_{13}$ are selected from unsubstituted or substituted alkyl, alkenyl, alkynyl, cycloalkyl, aryl, heteroaryl, or $R_{12}$ and $R_{13}$ when alkyl may be combined to form a 5–8 membered ring which may be substituted with 1–4 lower alkyl groups.

The term "substituted sulfamyl" is used to denote a radical having the formula —SO₂NR₁₂R₁₃, wherein $R_{12}$ and $R_{13}$ are as defined above.

The term "alkylene" refers to a divalent $C_1$–$C_{20}$ aliphatic hydrocarbon moiety, either straight or branched-chain, and either unsubstituted or substituted with one or more groups selected from alkoxy, halogen, aryl, or aryloxy.

The term "acyl" refers to a group of the formula R°C(O)—O—, wherein R° is preferably a $C_1$–$C_{20}$ alkyl moiety. The term "alkyl sulfonyl" refers to a group of the formula R° SO₂—, wherein R° is as defined for acyl.

Typical alkyl groups include methyl, ethyl, propyl, isopropyl, n-butyl, isobutyl, sec-butyl, tert-butyl, n-pentyl, isopentyl, neopentyl, n-hexyl, isohexyl, heptyl, octyl, nonyl, 2-ethylhexyl, decyl, undecyl, dodecyl, tetradecyl, hexadecyl, octadecyl and eicosyl.

Typical cycloalkyl groups include cyclopentyl, cyclohexyl, cycloheptyl, 2,3 and 4-methylcyclohexyl, 3,4-dimethylcyclohexyl, 3,5-dimethylcyclohexyl and menthyl(2-isopropyl-5-methylcyclohexyl).

Typical aryl groups include phenyl, naphthyl, 2,3 and 4-methylphenyl, 2,3 and 4-ethylphenyl, 4-isopropylphenyl, 2-n-propylphenyl, 4-n-butylphenyl, 4-sec-butylphenyl, 4-tert-butylphenyl, 2,6-diethylphenyl, 2-ethyl-6-methylphenyl, 2,4,6-trimethylphenyl, 4-n-pentylphenyl, 4-octylphenyl, 4-cyclohexylphenyl, 4-dodecylphenyl, 4-hexyloxyphenyl, 4-n-butoxyphenyl, 4-n-butoxycarbonylphenyl, 4-hexyloxycarbonylphenyl, 4-isobutyloxyphenyl, 4-hexanoyloxyphenyl and 4-(2-ethyl-hexyloxy)phenyl.

Typical —X-R groups include those listed in Table 1 below.

Two general routes are available for the synthesis of the NIRF compounds of Formula I. Route I involves the reaction of substituted phthalonitriles VI containing one or more leaving groups Z with one or more nucleophiles VII (A. W. Snow and J. R. Griffith, Macro-molecules, 1984, 17 (1614–1624), in the presence of a high boiling polar solvent such as N,N-dimethyl-formamide, N,N-dimethylacetamide, N-methyl-2-pyrrolidinone, tetramethylurea, and hexamethylphospho-triamide to give intermediates VIII, which are further reacted by known procedures to give compounds I directly in a one-pot process or to give the isoindoline derivatives IX, which are converted into the desired phthalocyanines I by known processes.

Route 1

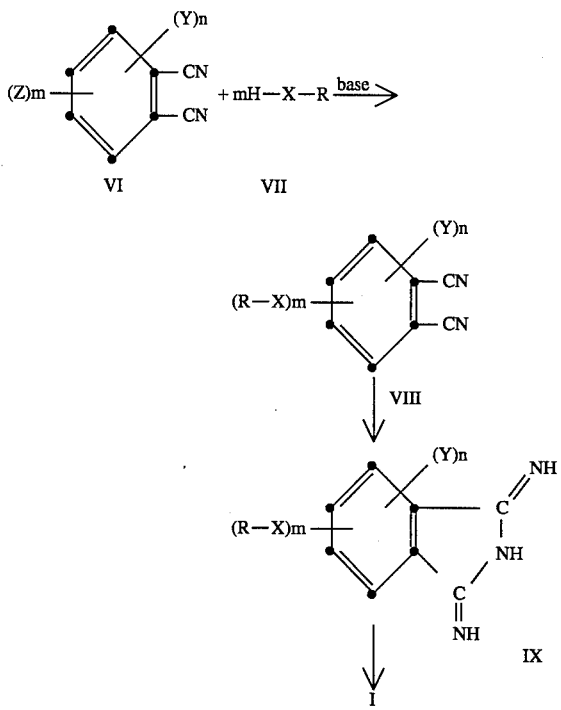

Of course, the starting compounds VI may contain further substituents which are not replaced by reaction with the nucleophile. Route 2 employs similar reaction conditions, as involved in initial step of Route 1, and makes use of the reactivity of the halogen atoms in polyhalo phthalocyanines X, containing 4–16 halogen atoms attached at peripheral carbon atoms, with nucleophiles VII (see U.K. Patent No. 1,537,375 and U.S. Pat. No. 4,606,859) to give NIRF compounds I.

Route 2

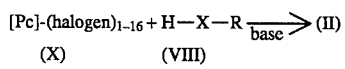

In the above nucleophilic reactions utilized in Routes 1 and 2, the base, or acid binding agent, may be an alkali metal hydroxide, an alkali metal bicarbonate or an alkali metal carbonate. For example, sodium carbonate, potassium carbonate, lithium hydroxide, sodium hydroxide, sodium bicarbonate and suitable bases.

The 2,3-naphthalocyanines of Formula II can be prepared by reacting 2,3-naphthalene-dicarbonitrile compounds XI to give 1,3-diiminobenz[f]-isoindolines XII, which are then converted to the naphthalocyanines of Formulae II by known procedures [J.A.C.S. 1984, 106, 7404–7410; U.S. Pat. No. 5,039,600, incorporated herein by reference; Zn. Obshch. Khim, 1972, 42(3), 696-9 (CA 77: 141469m); and Jap. Pat. 61,215,663 (CA 106:86223s)].

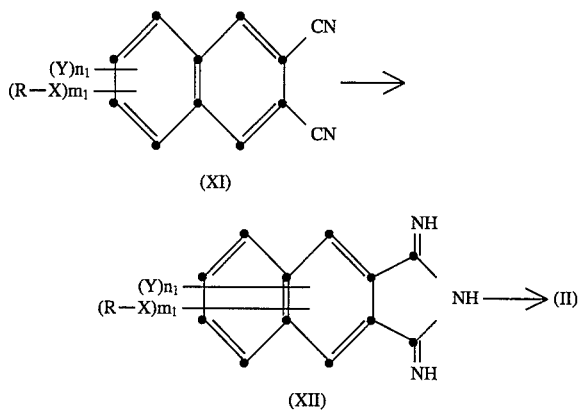

Intermediate compounds XI which contain one or more electron donating groups (—X–R) are conveniently prepared by reacting intermediate 2,3-naphthalenecarbonitriles XIII

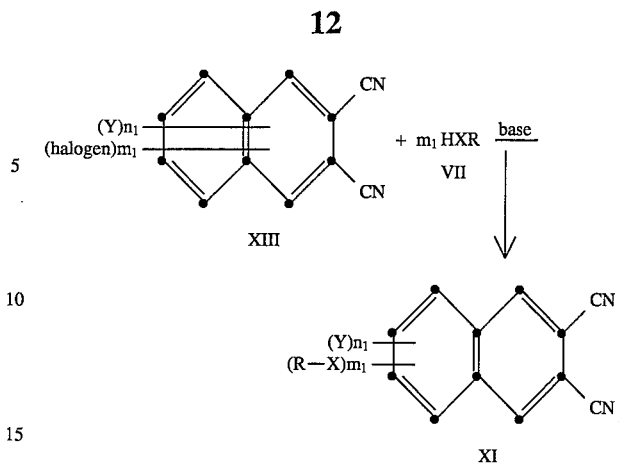

containing replaceable halogens with one or more nucleophiles under reaction conditions which favor nucleophilic displacements (J. Heterocyclic Chem. 1990, Vol. 27, Iss. 7, pp 2219–20).

The squaraines of Formula III can be prepared by reacting the corresponding unsubstituted and substituted 1,3-dihydro-2-methylene-1,1-dimethyl-1H-benz[e]indoles with squaric acid IS. Cohen, et al., JACS, 81, 3480 (1959)]. The reactions of squaric acid are well known in the art [R. West, editor, OXOCARBONS, Academic Press, New York, 1980, pp 185–231; G. Maahs and P. Hagenberg, Angew. Chem. internat. Edit., Vol. 5 (1966), No. 10, p 888; A. H. Schmidt, Synthesis, December 1980, p, 961]. The intermediate 1,3-dihydro-2-methylene-1,1-dimethyl-H-benz[e]indoles XIV can be synthesized by known procedures [U.S. Pat. No. 5,030,708, incorporated herein by reference]. The synthetic route is illustrated as follows:

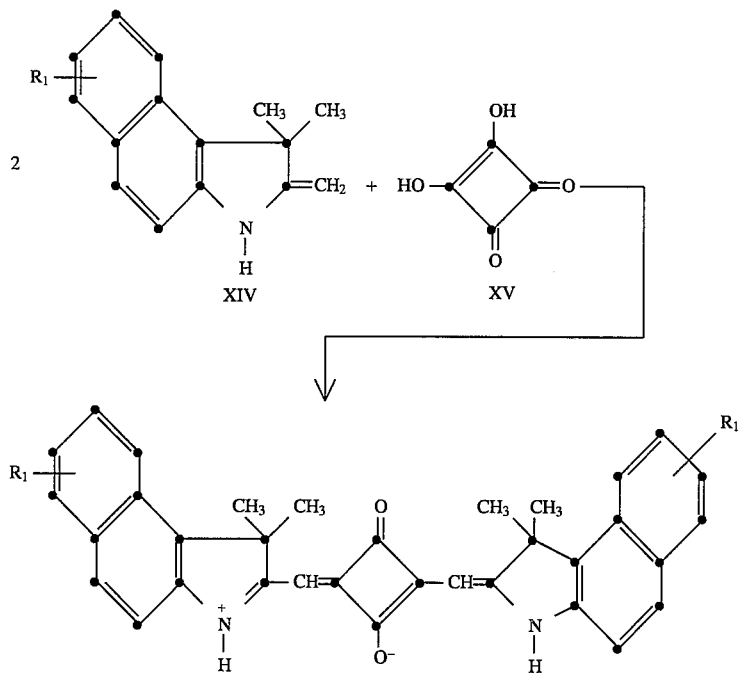

Intermediate 1,3-dihydro-2-methylene-1,1-dimethyl-H-benz[e] indoles XIV are reacted with squaric acid XV as shown to produce the squaraines. Of course, an unsymmetrical derivative is obtained as one of the components of the mixture prepared by reacting a mixture of two or more different intermediate benz[e]indole compounds XIV with squaric acid.

Croconic acid derivatives IV are prepared by the same procedure as the squaraines, except that croconic acid is used instead of squaric acid.

The preferred compounds which are useful in the practice of the invention contain one or a multiplicity of hydrocarbon moieties which can impart adequate solubility in the petroleum hydrocarbons. Usually the hydrocarbon moieties contain at least one straight or branched chain $C_4$–$C_{20}$ groups, which may be in combination with one or more aryl or cycloalkyl groups. In general, if only one or two hydrocarbon moieties are present the alkyl portion of the moiety should contain at least eight carbon atoms.

A convenient method for introducing adequate hydrocarbon moieties into the infrared fluorophore structure is to react infrared fluorophores (FL) containing electron deficient functional groups such as carboxy, carbonyl chloride, carbalkoxy or sulfonyl chloride with hydrocarbon rich compounds which contain electron rich groups such as alcohols and amines to give the corresponding esters and amides. Or, on the contrary, one can react infrared fluorophores (FL) containing functional amines and hydroxy groups with hydrocarbon rich compounds which contain functional groups such as carboxy, carbonyl chloride, carbalkoxy or sulfonyl chloride. Preferably, the carbalkoxy groups should be lower carbalkoxy, e.g. carbomethoxy, to promote easier transesterification.

be removed. Reactions 2, 3 and 4 are normally performed in the presence of base to facilitate completion of the reaction. Such bases include alkali metal carbonates, alkali metal bicarbonates, amines, e.g. trialkylamines and pyridine. To promote the formation of fluorophores having optimum solubility it is desirable that they be largely amorphous and to have low melting points or even be liquids. One method to accomplish this desired feature is to intentionally produce mixtures of fluorophores, preferably containing a high degree of branching in the alkyl portion of the hydrocarbon moiety.

The following examples illustrate further the synthetic methods which are used in preparing the compounds which are useful in the practice of the invention.

Experimental Section

EXAMPLE 1

A mixture of methyl 1,1,2-trimethyl-1H-benz[e]-indole-7-carboxylate (tautomer is methyl 1,3-dihydro-2-methylene-1,1-dimethyl-1H-benz [e]indole-7-carboxylate), 2.67 g (0.01 m) (see U.S. Pat. No. 5,030,708), squaric acid (0.57 g, 0.005 m) and 2-ethoxyethanol (40 g) was heated at reflux under nitrogen for 16 hours. The reaction mixture was cooled with an ice bath and the green solid collected by filtration, washed with isopropanol and dried in air. Recrystallization from 2-ethoxyethanol (20 mL), collection of the solid by filtration, washing of the solid with isopropanol and drying gave the pure product. Mass spectrometry indicated mostly the following structure plus a small amount

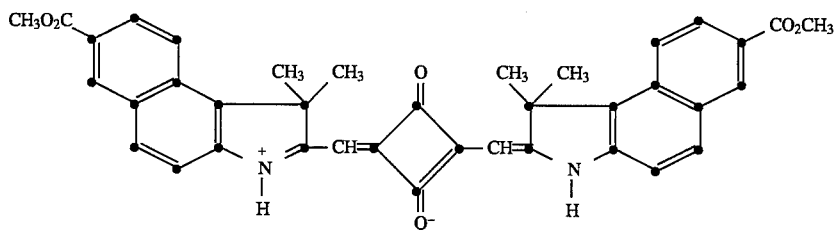

λ max - 690nm ($CH_2Cl_2$)

Typical reactions include the following:

1. $[FL]-(CO_2CH_3)_n \xrightarrow[\text{catalyst}]{Z-OH} [FL]-(CO_2Z)_n$ ester

2. $[FL]-(COCl)_n \xrightarrow[\text{base}]{Z-NH_2} [FL]-(CONHZ)_n$ amide

3. $[FL]-(OH)_n \xrightarrow[\text{base}]{Z-COCl} [FL]-(OCOZ)_n$ ester

4. $[FL]-(NH_2)_n \xrightarrow[\text{base}]{Z-COCl} [FL]-(NHCOZ)_n$ amide wherein n is 1–8 and Z is a hydrocarbon rich moiety. Reaction 1 may be conveniently carried out by heating the infrared fluorophore which contains the carbomethoxy group(s) with excess hydrocarbon rich alcohol(s), ZH, in the presence of a transesterification catalyst such as titanium IV isopropoxides while allowing the methanol thus formed to of the mono 2-ethoxyethyl ester which had been produced by transesterification. In methylene chloride an absorption maximum (A max) was observed in the visible-near infrared absorption spectrum at 690 nm (ε—214, 287).

EXAMPLE 2

A mixture of methyl 1,1,2-trimethyl-1H-benz[e]-indole-7-carboxylate (tautomer is methyl 1,3-dihydro-2-methylene-1,1-dimethyl-1H-benz[e]-indole-7-carboxylate) [2.67 g (0.01 m)], croconic acid trihydrate, (0.98 g, 0.005 m) and 2-ethoxyethanol (40 g) was heated at reflux under nitrogen for 16 hours. After allowing to cool, the reaction mixture was filtered and the solid was washed with methanol and dried in air (yield 2.2 g). The product was reslurried in boiling methanol, collected by filtration, washed with methanol and dried in air (yield—2.13 g). Mass spectrometry indicated mostly the following structure:

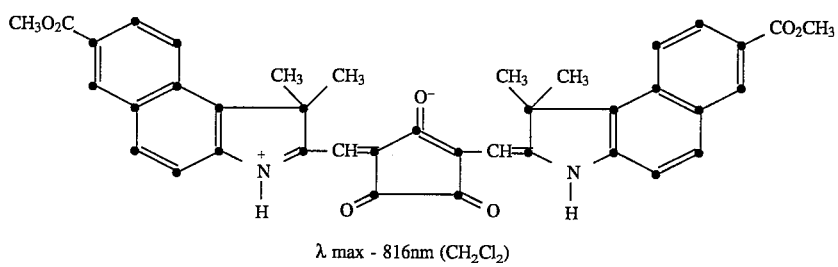

λ max - 816nm (CH₂Cl₂)

In methylene chloride an absorption maximum (λ max) was observed in the visible—near infrared absorption spectrum at 816 nm.

EXAMPLE 3

A mixture of methyl 1,1,2-trimethyl-1H-benz[e]-indole-7-carboxylate (tautomer is methyl 1,3-dihydro-2-methylene-1,1-dimethyl-1H-benz[e]-indole-7-carboxylate) [2.67 g (0.01 m)], squaric acid (0.57 g, 0.005 m), 2-ethylhexanol (30 g) and 2 drops of titanium IV isopropoxide was heated at reflux under nitrogen for 6 hours. The excess alcohol was removed by heating on a steam bath under vacuum. A solid was produced by treating the residue with hexane (some solubility) and was collected by filtration, washed with petroleum ether and dried in air (yield 2.92 g).

Mass spectrometry and proton NMR supported the following structure:

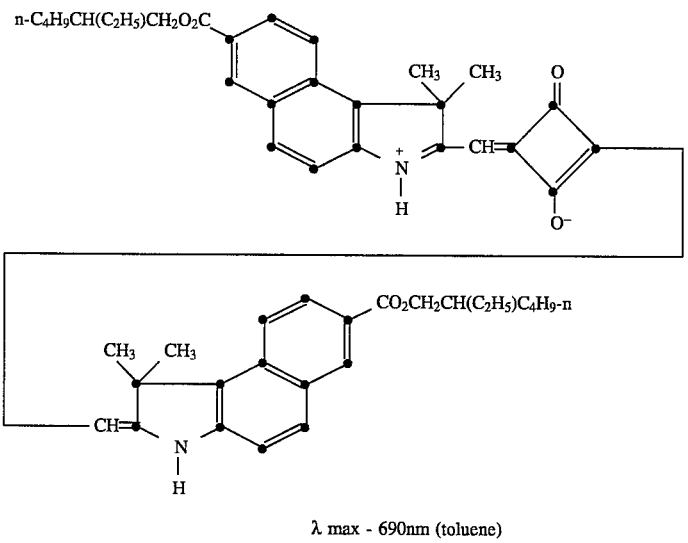

λ max - 690nm (toluene)

In toluene, an absorption maximum at 698 nm was observed in the near infrared absorption spectrum (E-192, 197).

EXAMPLE 4

A 300 mL 3-neck round-bottom flask was equipped with a magnetic stirrer, thermometer and gas inlet tube. Methanol (50 mL) was added followed by sodium metal (0.66 g, 0.029 mole) with stirring to facilitate reaction and solution, with a slow nitrogen purge applied. To this solution was added 12.54 g (0.058 mole) of 4-phenoxyphthalonitrile (A. W. Snow and J. R. Griffith, Macromolecules, 1984, 17, 1614–24), followed by additional methanol (50 mL). Anhydrous ammonia was bubbled in under the surface, giving an exotherm to 45° C. and total solution. The ammonia addition was continued until no more starting material was evident by thin-layer chromatography. The solution was clarified by filtering through a pad of Dicalite filter aid which had a small layer of charcoal on it and the filtrate drowned into water. The oily product layer thus produced was washed by decantation with 500 mL portions of water (4–5 times or until pH reached about 7–8). After the final wash water was decanted off, methanol was added to dissolve the product, which crystallized upon stirring overnight at room temperature. After being collected by filtration, the greenish-yellow solid was washed with methylene chloride and dried in air. The yield was 13.75 g, 91.1% of the theoretical yield. Mass spectrometry showed the product to consist largely of the desired 5-phenoxy-1,3-diiminoisoindoline.

EXAMPLE 5

A mixture of 5-phenoxy-1,3-diiminoisoindoline (3.68 g, 0.016 m) (from Example 4), 1,2,3,4-tetrahydro-aphthalene (20 mL) and tri-n-butylamine (10 mL) was stirred under a nitrogen sweep. Aluminum chloride (3.19 g, 0.024 m) was added to give a slurry. After the reaction mixture was heated at about 180° C. for 4 hours, it was allowed to cool to room temperature and diluted with methanol to enhance solubility to facilitate transfer into about 500 mL of ice-water mixture containing 10 mL HCl. The somewhat "greasy" solid product was collected by filtration and washed with dilute HCl. The filter cake was washed on the filter with cyclohexane and finally washed thoroughly with ethyl acetate and dried in air. Mass Spectrometry indicated good quality 2(3), 9(10), 16(17), 23(24)-tetraphenoxy-Pc-Al-Cl (Pc=phthalocyanine moiety) having the desired molecular weight of 942 (1.56 g, 41.4% of the theoretical yield).

EXAMPLE 6

A portion (110 mg) of the tetraphenoxy-chloroluminumphthalo-cyanine of Example 5 was dissolved in trifluoroacetic acid (10 mL) and allowed to evaporate at room temperature. As evidenced by mass spectrometry, the residual product was mostly 2(3), 9(10), 16(17), 23(24)-tetraphenoxy-Pc-AlOCOCF$_3$, molecular weight 1020. In methylene chloride, absorption maxima were observed at 696 nm ($\epsilon$—126,170), 629 nm ($\epsilon$—26,697), 341 nm ($\epsilon$—58,872) and 292 nm ($\epsilon$—30,600) in the ultraviolet, visible, near-infrared absorption spectra.

EXAMPLE 7

A reaction mixture of tetraphenoxy-chloroaluminum phthalocyanine (0.94 g) of Example 5, dimethyl-3-ydroxyisophthalate (0.24 g) and pyridine (20 g) was heated at reflux for 24 hours and allowed to cool to room temperature. Isopropanol (20 mL) was added and then by the addition of water, the phthalocyanine (Pc) product was precipitated, [2(3), 9(10), 16(17), 23(24)-tetraphenoxy-pc-AlOC$_6$H$_3$-3,5-di—CO$_2$CH$_3$], which was collected by filtration, washed with water and dried in air (yield—0.90 g). In methylene chloride, absorption maxima were observed at 696 nm (104,585), 626 nm (32,882) and 343 nm (64,090) in the ultraviolet, visible and near infrared absorption spectra.

EXAMPLE 8

A mixture of 5-phenoxy-1,3-diiminoisoindoline (3.68 g, 0.016 mole), silicon tetrachloride (4.0 g, 0.024 mole) 1,2,3,4-tetrahydronaphthalene (20 mL) and tri-n-butylamine (10 mL) was heated under nitrogen at about 200° C. for 40 minutes, allowed to stir overnight at room temperature and reheated to 180° C. and held for about 2.0 hours. After cooling to room temperature, the reaction mixture was diluted with 30 mL of methanol, filtered, and the collected solid washed with methanol and dried in air (yield—2.71 g, 69.3% of the theoretical yield). Mass spectrometry supported the structure: 2(3), 9(10), 16(17), 23(24)-tetra-phenoxy-Pc—Si-(Cl)$_2$.

EXAMPLE 9

A mixture of the tetraphenoxy-dichlorosiliconphthalocyanine (0.49 g) of Example 8, methyl 4-hydroxy-benzoate (0.16 g) and pyridine (5 g) was heated at reflux for 3 hours under nitrogen. To the cooled reaction mixture were added isopropanol (20 mL) and then water (20 mL) with stirring. The product was collected by filtration, washed with water and dried in air. Mass spectrometry supports the structure: 2(3), 9(10), 16(17), 23(24)-tetraphenoxy-pc-Si-(OC$_6$H$_4$—4—CO$_2$CH$_3$)$_2$.

EXAMPLE 10

A mixture of silicon phthalocyanine dichloride (0.2 g) was dissolved in trifluoroacetic acid (10 mL) and the reaction mixture allowed to stand in a hood in an evaporating dish until all the excess trifluoroacetic acid had evaporated. Absorption maxima were observed at 691 nm ($\epsilon$—168,645), 659 nm ($\epsilon$—21,596), 622 nm ($\epsilon$—4,789), 356 nm ($\epsilon$—50,090) and 334 nm ($\epsilon$—44,608) in the ultraviolet-visible-near infrared absorption spectra. The product was assumed to be silicon phthalocyanine trifluroacetate [Pc-Si (OCOCF$_3$)$_2$].

EXAMPLE 11

A reaction mixture of Nc-Si(OH)$_2$ (1.5 g) (J.A.C.S. 1984, 106, 7404–7410), pyridine (150 mL) and chloro dimethylphenylsilane (10 mL) was heated at reflux for 5 hours and then allowed to cool. Some insolubles were filtered off and the filtrate stripped on a rotary evaporator under vacuum. Pentane (300 mL) was added to the residue to produce a solid upon stirring which was collected by filtration, washed with 50/50 acetone/water, then with pentane and dried in air. The solid (1.9 g) was reslurried in hot pentane (300 mL) and filtered hot. The solid thus obtained was washed with pentane and air dried (yield—1.5 g). Mass spectrometry supported the following structure Nc-Si[O-si (CH$_3$)$_2$C$_6$H$_5$]$_2$.

EXAMPLE 12

A mixture of 5-phenoxy-1,3-diminoiosindoline (11.04 g, 0,047 m), tetrahydronaphthalene (60 mL), and tri-n-butyl amine (30.0 mL) was stirred. Silicon tetra-chloride (12.0 g, 0.071 m) was then added and the reaction mixture was heated slowly to reflux and held for 4 hours. After allowing to cool, the reaction mixture was diluted with an equal volume of methanol. The product, 2(3), 9(10), 16(17), 23(24) tetraphenoxy-PcSiCl$_2$ was collected by filtration, washed with methanol, then washed with water and dried in air. The yield of product was 7.7 g.

EXAMPLE 13

A portion (7.0 g, 0.0072 m) of the product of Example 11, methyl 4-hydroxybenzoate (2.4 g, 0.016 m) and pyridine (150 mL) were mixed and heated at reflux with stirring for 20 hours. The reaction mixture was cooled and then drowned into 500 mL water. Added about 50 mL of saturated sodium chloride solution with stirring. The product was collected by filtration, washed with water and dried in air (yield—7.1 g). Mass spectrometry confirmed the product to be the desired product [2(3), 9(10), 16(17), 23(24) tetraphenoxy-PcSi-(OC$_6$H$_4$-4—CO$_2$CH$_2$)$_2$]. Absorption maxima were obtained at 649 nm and 691 nm in the light absorption spectrum in methylene chloride.

EXAMPLE 14

A mixture of 3-phenylnaphthalene-2,3-dicarboxylic acid anhydride (6.26 g, 0.023), urea (45.0 g), ammonium molybdate (0.10 g) and aluminum chloride (0.90 g, 0.006 m) was heated under nitrogen at about 250° C. with stirring for 2.0 hours. Heat was removed and the dark brownish-black solid transferred into boiling water with stirring. The product was collected by filtration, reslurried in dilute hydrochloric acid, filtered, reslurried in dilute ammonium hydroxide, filtered, reslurried in hot water and finally filtered, washed with water and dried in air (yield—5.0 g). The product was presumed to be 5(36), 9(14), 18(23), 27(32) tetraphenyl-NcAlCl (Nc= naphthalocyanine moiety).

EXAMPLE 15

A mixture of 3,6-di-n-butoxy phthalonitrile (2.50 g, 0.0092 m), urea (20.0 g), ammonium molybdate (0.1 g) and aluminum chloride (0.41 g, 0.003 m) was heated under nitrogen with stirring at 250° C. in a Belmont metal bath for 2.0 hours. The dark solid was removed, pulverized and then added to a dilute HCl solution and stirred. The product was then collected by filtration, reslurried in dilute ammonium hydroxide, filtered, washed with water and dried in air. The product was presumed to be 1,4,8,11,15,18,22,25-octa-n-butoxy-PcAlCl.

EXAMPLE 16

A mixture of 6-t-butyl-2,3-dicyanonaphthalene (23.4, 0.10 m), aluminum chloride (3.5 g) and urea (23.0 g) was heated at 218°–220° C. for 1.0 hour in a Belmont metal bath with stirring. The reaction mixture was allowed to cool and the solid was pulverized using a mortar and pestle and then slurried in 10% NaOH, collected by filtration, washed with methanol and dried in air (yield 10.3 g). Based on mass spectrometry, it was concluded that the product was a mixture of 2(3), 11(12), 20(21), 29(30)-tetra-t-butyl-NcAlCl and 2(3), 11(12), 20(21), 29(30)-tetra-t-butyl-NcAlOH.

EXAMPLE 17

A mixture of 3-[2-(carbo-n-pentoxy)phenylthio]-phthalonitrile (7.0 g, 0.02 m), urea (28.6 g, 0.47 m) and aluminum chloride (0.713 g, 0.0053 m) was stirred in a Belmont metal bath (230° C.). The reddish melt was stirred slowly until homogeneous, then rapidly at about 215°–225° C. for 10 minutes. Stirring and heating were continued under a stream of $N_2$ for about 1.25 hours. The reaction flask was removed from the metal bath and allowed to cool. The solid was removed from the flask, placed in conc. HCl, ground to a good slurry in a mortar and pestle, filtered and washed with boiling water. Finally, the dark green solid was placed in fresh conc. HCl, the mixture boiled and then the solid was collected by filtration, washed with hot water and dried in air. The product, 1(4), 8(11), 15(18), 22(25)-tetra[2-carbo-n-pentoxy)phenylthio]-PcAlCl, when dissolved in N,N-dimethylformamide had a maximum absorption at 714 nm in the light absorption spectrum.

EXAMPLE 18

A mixture of aluminum phthalocyanine chloride (5.0 g, 0.0087 m), dimethyl 5-hydroxyisophthalate (1.83 g, 0.0087 m) and pyridine (25 mL) was heated and stirred at reflux for about 18 hours under nitrogen and then after cooling was drowned into water (500 mL). The green solid was collected by filtration, washed with water (1 l) and air dried. The product, $PcAlOC_6H_3$-3,5-$diCO_2CH_3$, had an absorption maximum at 675 nm (ε—198,481) in the light absorption spectrum in N,N-dimethylformamide.

EXAMPLE 19

A mixture of 4-phenylthiophthalonitrile (2.36 g, 0.01 m), aluminum chloride (0.35 g, 0.0026 m), ammonium molybdate (0.10 g) and urea (40.0 g) was placed in a flask and heated in a Belmont metal bath at about 200° C. with stirring for 2.5 hours at about 245° C. The flask was removed from the metal bath and allowed to cool. The solid was ground in a mortar and pestle, added to hot water, collected by filtration, washed with hot water, 5% HCl, dilute $NH_4OH$, hot water, 10% HCl, warm water and air dried (yield 2.50 g, 99.4% of the theoretical yield). An absorption maximum was observed at 701 nm in the light absorption spectrum of the product, 2(3), 9(10), 16(17), 23(24)-tetraphenylthio-PcAlCl, when dissolved in N,N-dimethylformamide.

EXAMPLE 20

A mixture of a portion (2.33 g, 0.0023 m) of the product of Example 19, dimethyl 5-hydroxyisophthalate (0.49 g, 0.0023 m) and pyridine (25 g) was heated and stirred at reflux under $N_2$ for 16 hours and then allowed to cool. The product [2(3), 9(10), 16(17), 23(24)-tetraphenylthio-$AlOC_6H_3$-3,5-$diCO_2CH_3$] was isolated by drowning into water (500 mL) and collecting by filtration and was then washed with water, acetone and methanol and dried in air. Attempts to obtain light absorption spectrum failed because of insolubility of the product.

EXAMPLE 21

A mixture of aluminum naphthalocyanine chloride (0.98 g, 0.00126 m) (Aldrich Chemical Co.), dimethyl 5-hydroxyisophthalate (0.21 g, 0.001 m), potassium carbonate (0.09 g) and dimethyl sulfoxide (23 g) was heated and stirred under $N_2$, at 95°–100° C. for about 8 hours. Very little solution of reactants seemed to have occurred. Added pyridine (23 mL) and heated at reflux under $N_2$ for about 96 hours (over the weekend). The green reaction mixture was allowed to cool and then drowned in water. The product (NcAl-$OC_6H_3$-3,5-di-$CO_2CH_3$) was collected by filtration, washed with water, reslurried in water, collected again by filtration, washed with water and dried in air (yield—0.94 g, 79.0% of the theoretical yield. An absorption maximum at 779 nm was observed in the light absorption spectrum in dimethyl sulfoxide.

EXAMPLE 22

A mixture of silicon naphthalocyanine dichloride (0.20 g, $2.46 \times 10^{-4}$ m), methyl 4-hydroxybenzoate (0.075 g, $4.93 \times 10^{-4}$ m), dimethyl sulfoxide (11.4 g) and pyridine (10.5 g) was heated and stirred under $N_2$ at reflux for about 64 hours. The reaction mixture was drowned into ice water mixture and the product [NcSi($OC_6H_4$-4—$CO_2CH_3$)$_2$] was collected by filtration, washed with water and dried in air. An attempt to obtain the absorption maximum in dimethyl sulfoxide (very slightly soluble) gave an apparent maximum at 773 nm in the light absorption spectrum.

EXAMPLE 23

A portion (2.0 g) of the product of Example 16 was added to conc. HCl (200 mL) and the mixture refluxed for 24.0 hours. The product 2(3), 11(12), 20(21), 29(30)-tetra-t-butylNcAlCl, was collected by filtration, washed with conc. HCl, washed with water and dried in air. An absorption maximum at 779 nm was observed in the light absorption spectrum in N,N-dimethylformamide.

EXAMPLE 24

A mixture of 3-phenoxyphthalonitrile (4.4 g, 0.02 m), aluminum chloride (0.8 g, 0.005 m) was placed in a Belmont metal bath at 250° C. and heated with stirring for 30 minutes under a nitrogen sweep. The reaction mixture was allowed to cool and the solid product was ground using a mortar and pestle and then slurried in hot water (500 mL) with stirring. After being collected by filtration, the product [1(4), 8(11), 15(18), 22(25)-tetraphenoxy-PcAlCl] was washed with boiling water (1 l), washed with cyclohexane, washed with n-hexane and dried in air (yield—4.3 g, 91.3% of the theoretical yield). An absorption maximum was observed at 700 nm in the light absorption spectrum in N,N-dimethylformamide.

EXAMPLE 25

A portion (2.0 g, 0.002 m) of the product of Example 24, dimethyl 5-hydroxyisophthalate (0.5 g, 0.002 m) and pyridine (100 mL) were mixed and heated with stirring at reflux for 24 hours. The reaction mixture was drowned into water and the solid was collected by filtration, washed with cyclohexane, washed with n-hexane and dried in air (yield 2.1 g, 94.2% of the theoretical yield). The product [1(4), 8(11), 15(18), 22(25)-tetraphenoxy-PcAlOC$_6$H$_3$-3,5-diCO$_2$CH$_3$] had an absorption maximum at 699 nm in the light absorption spectrum in N,N-dimethylformamide.

EXAMPLE 26

A mixture of 3-phenylthiophthalonitrile (11.8 g, 0.05 m) aluminum chloride (1.8 g, 0.014 m) was heated in a Belmont metal bath under a nitrogen sweep at about 250° C. for 1 hour. The reaction mixture was allowed to cool and the solid was ground in a mortar and pestle and then slurried by stirring in a warm 6% HCl aqueous solution. The product [1(4), 8(11), 15(18), 22(25)-tetraphenylthio-PcAlCl] was collected by filtration washed with warm water, washed with 6% HCl solution, washed with warm water and dried in air. Field desorption mass spectrometry showed a molecular ion of 1006, which supports the expected structure. An absorption maximum at 724 nm (ε—114,724) was observed in the light absorption spectrum in N,N-dimethyl-formamide.

EXAMPLE 27

A portion (5.03 g 0.005 m) of the product of Example 26, dimethyl 5-hydroxyisophthalate (1.05 g, 0.005 m) and pyridine (250 mL) were mixed and heated at reflux for 48 hours. The cooled reaction mixture was then drowned into water and the solid product was washed with warm water and dried in air (yield—5.4 g). A portion (1.5 g) of the product was dissolved in tetrahydrofuran (25.0 mL) and the solution placed on a column of activated aluminum oxide (150 mesh) (Aldrich Chem. Co.) and then eluted with methylene chloride to remove a fast moving band. The remaining product was eluted with methanol and then the methanol was removed by evaporation (yield—0.72 g). Field desorption mass spectrometry supported the desired product, 1(4), 8(11), 15(18), 22(25)-tetraphenylthio-pcAlOC$_6$H$_3$-3,5-diCO$_2$CH$_3$. An absorption maximum was observed at 729 nm (ε—128,526) in the light absorption spectrum of the chromatographed product in N,N-dimethylformamide.

EXAMPLE 28

A mixture of 6-t-butyl-1,3-diiminobenz(b) isoindoline (15.0 g, 0.06 m) silicon tetrachloride (10.8 mL), tetrahydronaphthalene (100.0 mL) and tributylamine (40.0 mL) was heated to reflux over a 1.0 hour period. After being refluxed for 3.0 hours, the reaction mixture was allowed to cool and then was treated with isopropanol (400 mL). The mixture was then drowned into water (1.0 l) and the solid [2(3), 11(12), 20(21), 29(30)-tetra-t-butyl-NcSiCl$_2$] was collected by filtration, washed with water and dried in air (yield—12.0 g). Absorption maxima were observed at 777 nm and 835 nm in the light absorption spectrum in N,N-dimethylformamide.

EXAMPLE 29

A mixture of 3-nitrophthalonitrile (8.65 g, 0.05 m), aluminum chloride (1.67 g, 0.0125 m) was heated in a Belmont metal bath under a nitrogen sweep at about 250° C. for 1 hour. The reaction mixture was allowed to cool and the solid was ground in a mortar and pestle and then slurried in a warm 6% HCl aqueous solution. The product [1(4), 8(11), 15(18), 22(25)-tetranitro-PcAlCl] was collected by filtration, washed with warm water, washed with 6% HCl solution, washed with warm water and dried in air.

EXAMPLE 30

A mixture of 2-3-dicyano-5-nitronaphthalene (8.9 g, 0.04 m), aluminum chloride (1.33 g, 0.01 m) was heated in a Belmont metal bath under a nitrogecn sweep at about 250° C. for 1 hour. The reaction mixture was allowed to cool and the solid was ground in a mortar and pestle and then slurried in a warm 6% HCl aqueous solution. The product [1(4), 10(13), 19(22), 29(31)-tetranitro-NcAlCl] was collected by filtration, washed with warm water, washed with 6% HCl solution, washed with warm water and dried in air.

EXAMPLE 31

A stock solution of the infrared fluorophore of Example 3 in toluene was prepared by dissolving 0.0089 g of fluorophore in 100 g of toluene (0.089 g/L, 890×10$^{-4}$ g/L). Dilutions of 1/25, 1/100, 1/200 and 1/1000 to give concentrations of 356×10$^{-5}$ g/L, 890×10$^{-6}$ g/L, 445×10$^{-6}$ g/L and 890×10$^{-7}$ g/L (8.9×10$^{-5}$ g/L) were made. At the lower concentration levels color was invisible to the eye. When exposed to light generated by a laser diode at 670 nm all of the samples had detectable fluorescence with a detector designed to detect infrared radiation having wavelengths in the 700–720 nm range.

EXAMPLE 32

The stock solution of Example 31 was diluted at the ratio of 1/25, 1/100, 1/200 and 1/1000 using premium grade gasoline to produce concentrations of 356×10$^{-5}$ g/L, 890×10$^{-6}$ g/L, 445×10$^{-6}$ g/L and 890×10$^{-7}$ g/L (8.9×10$^{-5}$ g/L). No color was observable in the samples having the lower concentrations. When exposed to light generated by a laser diode at 670 nm all of the samples had detectable fluorescence with a detector designed to detect infrared radiation having wavelengths in the 700–720 nm range. Upon standing several days none of the infrared fluorophores had settled or crystallized out even in the higher concentrations.

TABLE 1

EXEMPLARY —X—R GROUPS

| —X—R | —X—R |
|---|---|
| OCH$_2$CH(CH$_3$)$_2$ | —S—C(=N—)—S— attached to benzene ring with C(CH$_3$)$_3$ substituent (benzothiazole with t-butyl) |
| —OC$_4$H$_9$-n | —S— attached to pyridine ring bearing two CH$_3$ groups (lutidinyl) |
| —OC(CH$_3$)$_3$ | —S—C(=N—N=)—C$_6$H$_{11}$ (thiadiazole with cyclohexyl), S in ring |
| —OC$_{12}$H$_{25}$-n | —S—C(=N—N(C$_2$H$_4$OCOC$_3$H$_7$-n)—CH=N—) (triazole derivative) |
| SCH$_2$CH(C$_2$H$_5$)C$_4$H$_9$-n | —S—C(=N—)—O— benzoxazole with CH(CH$_3$)$_2$ substituent |
| S(CH$_2$)$_{12}$OCOCH$_3$ | —S—C(=N—)—N(H)— benzimidazole with C$_6$H$_{11}$ substituent |
| —SC$_8$H$_{17}$-n | —S—C(=N—)—S— benzothiazole with OC$_4$H$_9$-n substituent |
| —OCH$_2$CH(C$_2$H$_5$)C$_4$H$_9$-n | —S—C(=N—N=)—C(CO$_2$CH$_2$CH(CH$_3$)$_2$) (oxadiazole with ester), O in ring |
| —OCH$_2$CH=CH$_2$ | —S—(phenyl)—OC$_3$H$_7$-n |
| —OCH$_2$CH=CH$_2$ | —Te—(phenyl)—C$_4$H$_9$-n |

TABLE 1-continued

EXEMPLARY −X−R GROUPS

| −X−R | −X−R |
|---|---|
| −SCH$_2$C$_6$H$_5$ |  −Se—⟨⟩—C(CH$_3$)$_3$ |
| −SCH$_2$CH(OCOC$_4$H$_9$-n)CH$_2$OCOC$_4$H$_9$-n | −OCH$_2$C$_6$H$_4$-4-COO(CH$_2$)$_6$CH$_3$ |
| −OCH$_2$C≡CH | −OC$_6$H$_4$-4-CH$_2$COO(CH$_2$)$_7$CH$_3$ |
| −N(C$_4$H$_9$-n)$_2$ | −OCH$_2$CH$_2$CO$_2$C$_4$H$_9$-n |
| −NHC$_6$H$_4$-4-C(CH$_3$)$_3$ | −OCH$_2$CH$_2$OCOCH$_2$CH(C$_2$H$_5$)C$_4$H$_9$-n |
| −N(C$_4$H$_9$-n)C$_6$H$_5$ | −OC$_6$H$_4$-4-OCH$_2$CH$_3$ |
| −N[C$_2$H$_4$OCO(CH$_2$)$_4$CH$_3$]$_2$ | −OC$_6$H$_4$-4-OCH$_2$CH$_2$OCOC$_4$H$_9$-n |
| −NHC$_6$H$_{11}$ | 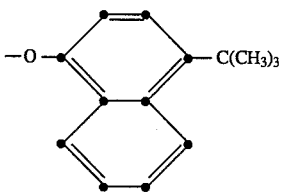 |
| −N(C$_4$H$_9$-n)C$_6$H$_{11}$ | |
| 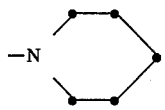 | 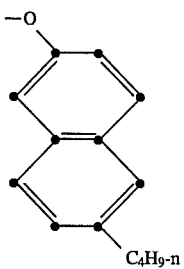 |
| −OC$_6$H$_5$ | −O(CH$_2$CH$_2$O)$_2$COC$_3$H$_7$-n |
| −OC$_6$H$_4$-4-COO(CH$_2$)$_{12}$CH$_3$ | −S(CH$_2$CH$_2$O)$_2$COC$_4$H$_9$-n |
| −SC$_6$H$_4$-4-COO(CH$_2$)$_{17}$CH$_3$ | −O(CH$_2$CH$_2$O)$_4$COCH$_2$CH(C$_2$H$_5$)C$_4$H$_9$-n |
| −OC$_6$H$_3$-3,5-diCOO(CH$_2$)$_7$CH$_3$ | −O(CH$_2$CH$_2$O)$_3$CH$_3$ |
| −OC$_6$H$_3$-3,5-diCO$_2$(CH$_2$)$_5$CH$_3$ | −O(CH$_2$CH$_2$O)$_2$C$_6$H$_5$ |
| −SC$_6$H$_4$-2-COOC$_4$H$_9$-n | −NH(CH$_2$CH$_2$O)$_2$CO(CH$_2$)$_{11}$CH$_3$ |
| −SC$_6$H$_4$-3-CO$_2$CH$_2$CH(CH$_3$)$_2$ | |
| −OC$_6$H$_4$-4-C$_2$H$_4$OCOC$_6$H$_{11}$ | |

TABLE 2

SQUARAINE COMPOUNDS

| EX. NO. | $R_1, R_2$ | $R_3, R_4$ | $R', R''$ |
|---|---|---|---|
| 33 | 7-$CO_2(CH_2)_3CH_3$ | $CH_3$ | $CH_3$ |
| 34 | 7-$CO_2C_2H_5$ | $C_6H_5$ | $CH_3$ |
| 35 | 7-$CO_2(C_6H_4$-4-$CH(CH_3)_2$ | $C_6H_4$-4-$CH_3$ | $CH_3$ |
| 36 | 7-$CONHCH_2CH(C_2H_5)C_4H_9$-n | H | $CH_3$ |
| 37 | 7-$CONHC_2H_4OCO(CH_2)_6CH_3$ | H | $CH_3$ |
| 38 | 7-$CON(CH_3)C_2H_4OCOCH_2CH(CH_3)_2$ | $CH_3$ | $CH_3$ |
| 39 | 7-$CON(CH_3)C_6H_{11}$ | H | $CH_3,CH_2CH_3$ |
| 40 | 7-$CONHC_6H_{11}$ | $C_4H_9$-n | $CH_2CH_3,CH_2CH_3$ |
| 41 | 7-$CONHC_6H_4$-4-$C_6H_{11}$ | H | $CH_3,CH_2CH(CH_3)_2$ |
| 42 | 7-$CONHCH_2C_6H_{10}$-4-$CH_2OH$ | $CH_3$ | $CH_3,CH_2CH_2CH(CH_3)_2$ |
| 43 | 7-$CONHC_6H_4$-4-$CO_2CH_3$ | H | $CH_3,CH(CH_3)_2$ |
| 44 | 7-$SO_2N(CH_3)(CH_2)_6CH_3$ | H | $CH_2CH(CH_3)_2,CH_2CH_3$ |
| 45 | 7-$SO_2N(C_4H_9$-n$)_2$ | $CH_3$ | $(CH_2)_5CH_3,(CH_2)_5CH_3$ |
| 46 | 7-$SO_2N(CH_3)C_6H_{11}$ | $CH_3$ | |
| 47 | 7-$SO_2N$⟨piperidine⟩ | H | $CH_3$ |
| 48 | 7-$SO_2N$⟨morpholine⟩ | H | $CH_3$ |

TABLE 2-continued

SQUARAINE COMPOUNDS

| EX. NO. | $R_1, R_2$ | $R_3, R_4$ | R', R" |
|---|---|---|---|
| 49 | 7-SO$_2$N(morpholine with CH$_3$ groups) | H | CH$_3$ |
| 50 | 7-SO$_2$NHCH$_2$C(CH$_3$)$_2$CH$_3$ | C$_6$H$_5$ | CH$_3$ |
| 51 | 7-SO$_2$NH(CH$_2$)$_{17}$CH$_3$ | H | CH$_3$ |
| 52 | 7-SO$_2$NHC$_6$H$_4$-3-CO$_2$(CH$_2$)$_6$CH$_3$ | H | CH$_3$ |
| 53 | 7-SO$_2$NHC$_6$H$_4$-4-(CH$_2$)$_{11}$CH$_3$ | CH$_3$ | CH$_3$ |
| 54 | 7-SO$_2$NHC$_6$H$_4$-3-CH$_2$OCO(CH$_2$)$_{10}$CH$_3$ | CH$_2$CH=CH$_2$ | CH$_3$ |
| 55 | 7-SO$_2$NHC$_6$H$_{10}$-4-CH$_3$ | H | CH$_3$ |
| 56 | 7-(CH$_2$)$_8$CH$_3$ | H | CH$_3$ |
| 57 | 7-(OC$_2$H$_6$-4-OCH$_2$CH(CH$_3$)$_2$ | H | CH$_3$ |
| 58 | 7-(OC$_2$H$_4$)$_3$OCH$_3$ | H | CH$_3$ |
| 59 | 7-S(CH$_2$)$_9$CH$_3$ | CH$_3$ | CH$_3$ |
| 60 | 7-SC$_6$H$_4$-4-C$_6$H$_{11}$ | H | CH$_3$ |
| 61 | 8-(CH$_2$)$_7$CH$_3$ | H | CH$_3$ |
| 62 | 8-OCH$_2$CH(C$_2$H$_5$)C$_4$H$_9$-n | H | CH$_3$ |
| 63 | 8-O(CH$_2$)$_{11}$CH$_3$ | H | CH$_3$ |
| 64 | 8-OCO(CH$_2$)$_6$CH$_3$ | H | CH$_3$ |
| 65 | 7-C$_6$H$_{11}$ | H | CH$_3$ |
| 66 | 7-COOC(CH$_3$)$_3$ | H | CH$_3$ |
| 67 | 7-CO$_2$(CH$_2$)$_3$CH(CH$_3$)$_2$ | H | CH$_3$ |
| 68 | 7-CO$_2$(CH$_2$)$_2$CH(CH$_3$)$_2$ | H | CH$_3$ |
| 69 | 7-CH$_2$CH(CH$_3$)CH$_2$C(CH$_3$)$_2$CH$_3$ | H | CH$_3$ |

TABLE 2-continued

SQUARAINE COMPOUNDS

| EX. NO. | $R_1, R_2$ | $R_3, R_4$ | R', R" |
|---|---|---|---|
| 70 | 7-CO$_2$-[thiophene ring with CH$_3$ and CH(CH$_3$)$_2$ substituents] | $C_6H_5$ | $CH_3$ |
| 71 | 7-SO$_2$C$_6$H$_4$-4-O(CH$_2$)$_3$CH(CH$_3$)$_2$ | H | $CH_3$ |
| 72 | 7-SO$_2$(CH$_2$)$_2$CH(CH$_3$)CH$_2$CH$_3$ | H | $CH_3$ |
| 73 | 7-SO$_2$(CH$_2$)$_{13}$CH$_3$ | H | $CH_3$ |
| 74 | 7-SO$_2$C$_6$H$_4$-3-CO$_2$(CH$_2$)$_{11}$CH$_3$ | H | $CH_3$ |
| 75 | CO$_2$CH$_2$-[thiophene ring with CH$_2$OCH$_3$] | H | $CH_3$ |
| 76 | CO$_2$CH$_2$-[thiophene ring with CH$_3$] | H | $CH_3$ |
| 77 | 7-NHSO$_2$(CH$_2$)$_{11}$CH$_3$ | $CH_3$ | $CH_3$ |
| 78 | 7-NHSO$_2$C$_6$H$_4$-4-CH$_2$CH$_3$ | H | $CH_3$ |
| 79 | 7-NHSO$_2$C$_6$H$_{11}$ | H | $CH_3$ |
| 80 | 7-N(C$_6$H$_{11}$)SO$_2$(CH$_2$)$_5$CH$_3$ | $CH_3$ | $CH_3$ |
| 81 | 7-Sn(CH$_3$)$_3$ | H | $CH_3$ |
| 82 | 7-Sn(OCH$_2$CH$_3$)$_3$ | H | $CH_3$ |
| 83 | 7-Si(CH$_3$)$_2$C$_6$H$_5$ | H | $CH_3$ |
| 84 | 7-Si(OC$_4$H$_9$-n)$_3$ | H | $CH_3$ |

TABLE 2-continued
SQUARAINE COMPOUNDS
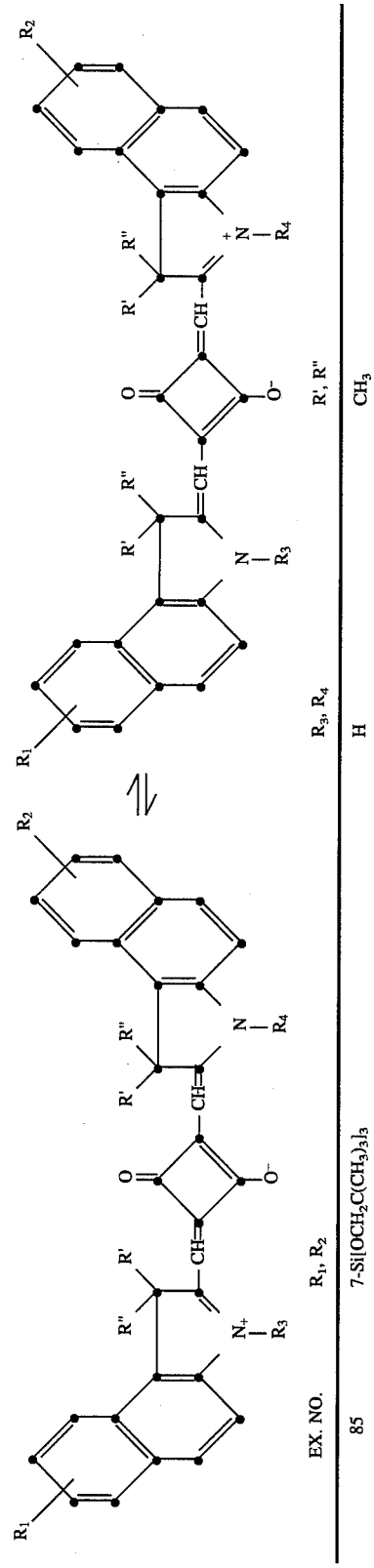
| EX. NO. | $R_1, R_2$ | $R_3, R_4$ | $R', R''$ |
|---|---|---|---|
| 85 | 7-Si[OCH$_2$C(CH$_3$)$_3$]$_3$ | H | CH$_3$ |

TABLE 3

PHTHALOCYANINE COMPOUNDS
(Pc = PHTHALOCYANINE NUCLEUS)

| EX. NO. | COMPOUND |
|---|---|
| 86 | 1(4), 8(11), 15(18), 22(25)-Tetra[4(2-ethylhexyloxycarbonyl)phenylthio]PcH$_2$ |
| 87 | 2(3), 9(10), 16(17), 23(24)-Tetraphenoxy-PcAl—OC$_6$H$_4$-4-CO$_2$CH$_2$CH(C$_2$H$_5$)C$_4$H$_9$-n |
| 88 | 2(3), 9(10), 16(17), 23(24)-Tetraphenoxy-PcAl—SC$_6$H$_4$-2-CO$_2$(CH$_2$)$_3$CH(CH$_3$)$_2$ |
| 89 | 2(3), 9(10), 16(17), 23(24)-Tetraphenoxy-PcAl—S—C$_6$H$_4$-2-CO$_2$C$_4$H$_9$-n |
| 90 | 2(3), 9(10), 16(17), 23(24)-Tetraphenoxy-PcAlOC$_6$H$_4$-4-C$_6$H$_{11}$ |
| 91 | 2(3), 9(10), 16(17), 23(24)-Tetra-(4-n-butoxyphenoxy)-PcAlOCOCF$_3$ |
| 92 | 2(3), 9(10), 16(17), 23(24)-Tetra-(4-nonylphenoxy)PcH$_2$ |
| 93 | 2(3), 9(10), 16(17), 23(24)-Tetra-(4-t-butylphenylthio)-PcH$_2$ |
| 94 | 2(3), 9(10), 16(17), 23(24)-Tetra-(4-isoamylphenylthio)-PcZn |
| 95 | 2(3), 9(10), 16(17), 23(24)-Tetra-(4-n-hexylphenoxy)-PcSiCl$_2$ |
| 96 | 2(3), 9(10), 16(17), 23(24)-Tetra-[4-(2-ethylhexyloxycarbonyl)-phenylthio]PcH$_2$ |
| 97 | 2(3), 9(10), 16(17), 23(24)-Tetra-(4-cyclohexylphenoxy)-PcSi(OCH$_2$CH$_2$OC$_4$H$_9$-n)$_2$ |
| 98 | 2(3), 9(10), 16(17), 23(24)-Tetra-(4-dodecylphenoxy)-PcSi(OC$_4$H$_9$-n)$_2$ |
| 99 | 2(3), 9(10), 16(17), 23(24)-Tetra-(4-undecylphenoxy)-PcSi(OCOCH$_3$)$_2$ |
| 100 | 2(3), 9(10), 16(17), 23(24)-Tetra-(4-tetradecylphenoxy)-PcH$_2$ |
| 101 | 2(3), 9(10), 16(17), 23(24)-Tetra-(4-octadecylphenoxy)-PcMg |
| 102 | 2(3), 9(10), 16(17), 23(24)-Tetra-(dodecylthio)-PcH$_2$ |
| 103 | 2(3), 9(10), 16(17), 23(24)-Tetra-(4-carbodecyloxyphenoxy)-PcH$_2$ |
| 104 | 2(3), 9(10), 16(17), 23(24)-Tetra-(2(carbononyloxyphenylthio)-PcSi(OH)$_2$ |
| 105 | 2(3), 9(10), 16(17), 23(24)-Tetrallyloxy-PcAlCl |
| 106 | 2(3), 9(10), 16(17), 23(24)-Tetra(2-ethylhexylamino)PcH$_2$ |
| 107 | 2(3), 9(10), 16(17), 23(24)-Tetracyclohexyloxy-PcSi[OC(C$_6$H$_5$)$_3$]1$_2$ |
| 108 | 2(3), 9(10), 16(17), 23(24)-Tetra(6-t-butylbenzothiazol-2-ylthio)-PcAlCl |
| 109 | 2(3), 9(10), 16(17), 23(24)-Tetra(6-isopropylbenzoxazol-2-ylthio)PcAlOCOCF$_3$ |
| 110 | 2(3), 9(10), 16(17), 23(24)-Tetra(5-n-hexyl-1,3,4-thiadiazol-2-ylthio)PcAlCl |
| 111 | 2(3), 9(10), 16(17), 23(24)-Tetra(4,6-di-methyl-2-pyridylthio)-PcSi(OC$_6$H$_4$-4-t-butyl)$_2$ |
| 112 | 2(3), 9(10), 16(17), 23(24)-Tetra(4-cyclohexylphenyl)telluro-PcSi(OH$_2$) |
| 113 | 2(3), 9(10), 16(17), 23(24)-Tetra(4-dodecylphenyl)seleno-PcAlCl |
| 114 | 2(3), 9(10), 16(17), 23 (24)-Tetra-n-octylthio-PcSi(OC$_6$H$_4$-4-F)$_2$ |
| 115 | 2(3), 9(10), 16(17), 23(24)-Tetra-(6-t-butyl-2-naphthylthio)-PcAlOH |
| 116 | 2(3), 9(10), 16(17), 23(24)-Tetradioctylamino-PcAlOCOCF$_3$ |
| 117 | 2(3), 9(10), 16(17), 23(24)-Tetrapiperidino-PcAlOH |
| 118 | 2(3), 9(10), 16(17), 23(24)-Tetratriazol-3-ylthio-PcSiCl$_2$ |
| 119 | 2(3), 9(10), 16(17), 23(24)-Tetratriazol-3-ylthio-PcH$_2$ |
| 120 | 2(3), 9(10), 16(17), 23(24)-Tetratriazol-3-ylthio-PcSi(OH)$_2$ |
| 121 | 2(3), 9(10), 16(17), 23(24)-Tetra[(2-ethylhexyloxy)anilino]-PcH$_2$ |
| 122 | 2(3), 9(10), 16(17), 23(24)-Tetra(4-dodecyloxyphenoxy)-PcH$_2$ |
| 123 | 2(3), 9(10), 16(17), 23(24)-Tetra(2-naphthyloxy)-PcH$_2$ |
| 124 | 2(3), 9(10), 16(17), 23(24)-Tetra(4-carboneopentyloxyphenylthio)-PcH$_2$ |
| 125 | 1,4,8,11,15,18,22,25-octahexyloxy-2,3,9,10,16,17,23,24-octachloro-PcSi(OH)$_2$ |
| 126 | 1,4,8,11,15,18,22,25-octa-n-butoxy-2,3,9,10,16,17,23,24-octachloro-PcH$_2$ |
| 127 | 1,4,8,11,15,18,22,25-octa-isohexyloxy-2,3,9,10,16,17,23,24-octachloro-PcH$_2$ |
| 128 | Hexadecamethyl-PcAlOH |
| 129 | Hexadecaanilino-PcSi(OH)$_2$ |
| 130 | Hexadeca(4-methylphenylthio)-PcSi(OC$_6$F$_5$)$_2$ |
| 131 | 1,4,8,11,15,18,22,25-Octabutoxy-PcH$_2$ |
| 132 | 1, 4,8,11,15, 18,22, 25-Octaphenylthio-PcSi[O—Si(CH$_3$)$_2$C$_6$H$_5$]$_2$ |
| 133 | 1,4,8,11,15,18,22,25-Octa-(4-n-hexyloxyphenoxy)-PcH$_2$ |
| 134 | 1,4,8,11,15,18,22,25-Octa-(4-t-butylphenylthio)-PcH$_2$ |
| 135 | 1,4,8,11,15,18,22,25-Octa-(4-octylthiophenylthio)PcSiCl$_2$ |
| 136 | 2,3,9,10,16,17,23,24-Octaethoxy-Pc—Al—OH |
| 137 | 2,3,9,10,16,17,23,24-Octa-(4-t-butylphenylthio)PcH$_2$ |
| 138 | 2,3,9,10,16,17,23,24-Octadecyloxy-Pc—SiCl$_2$ |
| 139 | 2,3,9,10,16,17,23,24-Octaphenylthio-PcSi(OC$_6$H$_5$)$_2$ |
| 140 | 2,3,9,10,16,17,23,24-Octa(12-acetoxydodecyloxy)PcSi[OC$_6$H$_4$-4-CO$_2$hexyl]$_2$ |
| 141 | 2,3,9,10,16,17,23,24-Octa(2-ethylhexyl)PcSi(OCOCF$_3$)$_2$ |
| 142 | 2,3,9,10,16,17,23,24-Octa(2-isooctylphenylthio)-PcAlOH |
| 143 | 2,3,9,10,16,17,23,24-Octa(t-butoxyphenoxy)-PcAlCl |
| 144 | 2,3,9,10,16,17,23,24-Octa(6-isopropylbenzothiazol-2-ylthio)PcAlOH |
| 145 | 1,4,8,11,15,18,22,25-Octa(3-methylbutoxy)-2,3,9,10,16,17,23,24-octaphenylthio-PcAlOH |
| 146 | 1,4,8,11,15,18,22,25-Octa(3-methylbutoxy)-2,3,9,10,16,17,23,24-octaphenoxy-PcSi(OH)$_2$ |
| 147 | 1,4,8,11,15,18,22,25-Octa(3-methylbutoxy)-2,3,9,10,16,17,23,24-octa-n-butylthio-PcAlOH |
| 148 | 1,4,8,11,15,18,22,25-Octa(3-methylbutoxy)-2,3,9,10,16,17,23,24-octa-4(t-butylphenylthio)PcAlCl |
| 149 | 1,4,8,11,15,18,22,25-Octafluoro-2,3,9,10,16,17,23,24-octaphenylthio-PcAlOC$_6$H$_4$-4-CO$_2$CH$_3$ |
| 150 | 1,4,8,11,15,18,22,25-Octafluoro-2,3,9,10,16,17,23,24-octaphenylthio-PcAlOH |
| 151 | 2(3), 9(10), 16(17), 23(24)-Tetra(N-cyclohexyl-N-decanylamino)-PcAlCl |
| 152 | 2(3), 9(10), 16(17), 23(24)-Tetra(3,5-di-t-butylphenoxy)PcH$_2$ |
| 153 | 2(3), 9(10), 16(17), 23(24)-Tetracyclohexanesulfonamido-PcAlOH |
| 154 | 2(3), 9(10), 16(17), 23(24)-Tetra[4-(carbo-2-ethylhexyloxy)phenoxy]PcH$_2$ |
| 155 | 2(3), 9(10), 16(17), 23 (24)-Tetra-[Si(CH$_3$)$_2$C$_6$H$_5$]—PcAlCl |
| 156 | 2(3), 9(10), 16(17), 23(24)-Tetra[Si(OCH$_3$)$_3$]—PcAlOH |
| 157 | 2(3), 9(10), 16(17), 23 (24)-Tetra[Sn(C$_4$H$_9$-n)$_3$]—AlCl |
| 158 | 2(3), 9(10), 16(17), 23(24)-Tetra[Sn(Oamyl)$_3$]—PcAlOH |

TABLE 3-continued

PHTHALOCYANINE COMPOUNDS
(Pc = PHTHALOCYANINE NUCLEUS)

| EX. NO. | COMPOUND |
| --- | --- |
| 159 | 2(3), 9(10), 16(17), 23(24)-Tetra[N-phenylbutanesulfonamido)-PcAlCl |
| 160 | 2(3), 9(10), 16(17), 23(24)-Tetra(N-octylbenzamido)-PcSi(OH)$_2$ |
| 161 | 2(3), 8(11), 15(18), 22(25)-Tetraamino-PcAlOH |
| 162 | PcAlOC$_6$H$_4$-4-CH$_2$CH$_2$OCOCH$_2$CH(C$_2$H$_5$)C$_4$H$_9$-n |
| 163 | PcAlOC$_6$H$_2$-3,5-di-CO$_2$octyl-4-NO$_2$ |
| 164 | 1,2,3,4,8,9,10,11,15,16,17,18,22,23,24,25-Hexadecyl(4-t-butylphenylthio)PcH$_2$ |
| 165 | 2(3), 9(10), 16(17), 23(24)-Tetra(3-pentadecylphenoxy)-PcH$_2$ |
| 166 | 2(3), 9(10), 16(17), 23(24)-Tetra(1,1-dimethylpropyl)-PcH$_2$ |
| 167 | 2(3), 9(10), 16(17), 23(24)-Tetra(1,1-dimethylpropyl)-PcAlOC$_6$H$_3$-3,5-di-CO$_2$cyclohexyl |
| 168 | 2(3), 9(10), 16(17), 23(24)-Tetra(n-dodecylthio)-PcAlOC$_6$H$_3$-3,5-di-CO$_2$-methyl |
| 169 | 1(4), 8(11), 15(18), 22(25)-Tetra-NHC$_8$H$_{17}$—PcH$_2$ |
| 170 | 1(4), 8(11), 15(18), 22(25)-Tetra-NHC$_{12}$H$_{25}$—PcH$_2$ |
| 171 | 1(4), 8(11), 15(18), 22(25)-Tetra-[N(COCF$_3$)C$_8$H$_{17}$]—PcAlCl |
| 172 | 1(4), 8(11), 15(18), 22(25)-Tetra-N(C$_8$H$_{17}$)$_2$—PcAlCl |

TABLE 4

NAPHTRALOCYANINE COMPOUNDS
(Nc = NAPHTHALOCYANINE NUCLEUS)

| EX. NO. | COMPOUND |
| --- | --- |
| 173 | 2(3), 11(12), 20(21), 29(30)-Tetra-t-butyl-NcH$_2$ |
| 174 | 2(3), 11(12), 20(21), 29(30)-Tetraisopentyl-NcAlOC$_6$H$_4$-4-CO$_2$CH$_3$ |
| 175 | 2(3), 11(12), 20(21), 29(30)-Tetraisobutyl-NcSi(OH)$_2$ |
| 176 | 2(3), 11(12), 20(21), 29(30)-Tetraisoamyl-NcAlOH |
| 177 | 2(3), 11(12), 20(21), 29(30)-Tetraoctyl-NcH$_2$ |
| 178 | 2(3), 11(12), 20(21), 29(30)-Tetraisohexyl-NcSi[OSn(C$_4$H$_9$—n)$_3$]$_2$ |
| 179 | 2(3), 11(12), 20(21), 29(30)-Tetraoctyl-NcSi[OGe[Ohexyl]$_3$]$_2$ |
| 180 | 2(3), 11(12), 20(21), 29(30)-Tetranonyl-NcSi(OCH$_2$CH$_2$CH$_2$OC$_4$H$_9$—n)$_2$ |
| 181 | 2(3), 11(12), 20(21), 29(30)-Tetra-(2,2,4-trimethylpentyl)-NcAlOC$_6$H$_4$-4-CO$_2$methyl |
| 182 | 2(3), 11(12), 20(21), 29(30)-Tetra-(2-ethylhexyl)-NcAlOC$_6$H$_3$-3,5-diCO$_2$dodecyl |
| 183 | 2(3), 11(12), 20(21), 29(30)-Tetra-t-butyl-NcSi(OC$_6$H$_4$-4-CO$_2$cyclohexyl)$_2$ |
| 184 | 2(3), 11(12), 20(21), 29(30)-Tetra-t-butyl-NcSi(OCO-t-butyl)$_2$ |
| 185 | 2(3), 11(12), 20(21), 29(30)-TetrapentadecylNcH$_2$ |
| 186 | 2(3), 11(12), 20(21), 29(30)-Tetra(hexadecyloxy)-NcH$_2$ |
| 187 | 2(3), 11(12), 20(21), 29(30)-Tetra-t-butyl-NcZn |
| 188 | 2(3), 11(12), 20(21), 29(30)-Tetrabenzyl-NcAlOH |
| 189 | 2(3), 11(12), 20(21), 29(30)-Tetra(2-ethylhexyloxy)-NcAlCl |
| 190 | NcSi(OCH$_2$CH$_2$CH$_2$OC$_4$H$_9$—n)$_2$ |
| 191 | NcSiOCO(CH$_2$)$_7$CH$_3$ |
| 192 | NcAl OCH$_2$C(CH$_3$)(CH$_3$)—CH$_2$CH$_3$ |
| 193 | 2(3), 11(12), 20(21), 29(30)-Tetra-[O—C$_6$H$_4$—CO$_2$(CH$_2$)$_2$CH$_3$]—NcAlCl |
| 194 | 2(3), 11(12), 20(21), 29(30)-Tetra-[OC$_6$H$_3$-3,5-diCO$_2$CH$_2$CH(CH$_3$)$_2$]NcAlOH |
| 195 | 2(3), 11(12), 20(21), 29(30)-Tetra[SC$_6$H$_4$-3-CO$_2$CH$_2$CH(CH$_3$)$_2$]—NcSi(OH)$_2$ |
| 196 | 2(3), 11(12), 20(21), 29(30)-Tetra-n-butoxy-NcSi[OSi(C$_6$H$_5$)$_3$]$_2$ |
| 197 | 2(3), 11(12), 20(21), 29(30)-Tetra-n-butoxy-NcSi[OCOC$_6$H$_{11}$]$_2$ |
| 198 | 2(3), 11(12), 20(21), 29(30)-Tetradodecyloxy-NcSi(OH)$_2$ |
| 199 | 2(3), 11(12), 20(21), 29(30)-Tetra(6-dodecyloxybenzothiazol-2-ylthio)-NcAlOH |
| 200 | 2(3), 11(12), 20(21), 29(30)-Tetra(6-hexylbenzimidazol-2-ylthio)-NcAlOCOCF$_3$ |
| 201 | 2(3), 11(12), 20(21), 29(30)-Tetra(t-butylphenylseleno)-NcAlCl$_2$ |
| 202 | 2(3), 11(12), 20(21), 29(30)-Tetra(n-butylphenyltelluro)-NcSiCl$_2$ |
| 203 | 2(3), 11(12), 20(21), 29(30)-Tetra(t-butylanilino)-NcSi(OH)$_2$ |
| 204 | 2(3), 11(12), 20(21), 29(30)-Tetra(6-n-butyl-2-naphthyloxy)-NcSi(OCOCF$_3$)$_2$ |
| 205 | 2(3), 11(12), 20(21), 29(30)-Tetra(6-neopentyl-2-naphthylthio)-NcSi(OCOCH$_3$)$_2$ |
| 206 | 2(3), 11(12), 20(21), 29(30)-Tetraallyloxy-Nc—AlOH |
| 207 | 2(3), 11(12), 20(21), 29(30)-Tetrapropargyloxy-NC—Si(OH)$_2$ |
| 208 | 2(3), 11(12), 20(21), 29(30)-Tetra(cyclohexyloxy)-NC—Si[OC$_6$H$_3$-3,5-diCO$_2$CH$_3$]$_2$ |
| 209 | 2(3), 11(12), 20(21), 29(30)-Tetra(2-phenoxyethoxy)-Nc—AlOH |
| 210 | 2(3), 11(12), 20(21), 29(30)-Tetra(2-phenylethoxy)-Nc—H$_2$ |
| 211 | 2(3), 11(12), 20(21), 29(30)-Tetra(benzyloxy)-Nc—AlOH |
| 212 | 2(3), 11(12), 20(21), 29(30)-Tetrapiperidino-Nc—Si(OH)$_2$ |
| 213 | 5,9,14,18,23,27,32,36-Octa(N-n-butyl-N-phenylamino)-NcSi(OH)$_2$ |
| 214 | 5,9,14,18,23,27,32,36-Octa(di-N,N-n-butylamino)-NcAlCl |

TABLE 4-continued

NAPHTRALOCYANINE COMPOUNDS
(Nc = NAPHTHALOCYANINE NUCLEUS)

| EX. NO. | COMPOUND |
|---|---|
| 215 | 5,9,14,18,23,27,32,36-Octa-n-butoxy-NcSi(OCCOCF$_3$)$_2$ |
| 216 | 5,9,14,18,23,27,32,36-Octa-n-butoxy-NcSi(OH)$_2$ |
| 217 | 5,9,14,18,23,27,32,36-Octaphenoxy-NcH$_2$ |
| 218 | 5,9,14,18,23,27,32,36-Octaallyloxy-NcAlOC$_6$H$_4$-4-CO$_2$menthyl |
| 219 | 5,9,14,18,23,27,32,36-Octa(octylthio)-NcAlCl |
| 220 | 2(3), 11(12), 20(21), 29(30)-Tetra(4-t-butylphenoxy)-NcAlOH |
| 221 | 2(3), 11(12), 20(21), 29(30)-Tetra(4-isoamylphenoxy)-NcAlCl |
| 222 | 2,3,11,12,20,21,29,30-Octa(4-cyclohexylphenoxy)-NcSi(OH)$_2$ |
| 223 | 2,3,11,12,20,21,29,30-Octa(hexadecyloxy)-NcAlOH |
| 224 | 2,3,11,12,20,21,29,30-Octa(octadecyloxy)-NcSi(OH)$_2$ |
| 225 | 2,3,11,12,20,21,29,30-Octa(icosanyloxy)-NcSi(OCOCF$_3$)$_2$ |
| 226 | 2,3,11,12,20,21,29,30-Octa(2-ethylhexyloxy)-NcAlCl |
| 227 | 2,3,11,12,20,21,29,30-Octa(undecanyloxy)-NcAlOH |
| 228 | 2,3,11,12,20,21,29,30-Octa(4-t-butoxyphenoxy)NcAlOH |
| 229 | 2,3,11,12,20,21,29,30-Octa(4-n-butoxyphenylthio)NcSi(OH)$_2$ |
| 230 | 2,3,11,12,20,21,29,30-Octa(2-ethylhexoxy)-NcSi(OH)$_2$ |
| 231 | 2,3,11,12,20,21,29,30-Octa[CH$_3$O(CH$_2$CH$_2$O)$_3$]—NcAlCl |
| 232 | 2,3,11,12,20,21,29,30-Octa[OCH$_2$CH$_2$OCOCH$_2$CH(C$_2$H$_5$)C$_4$H$_9$—n]NcSi(OH)$_2$ |
| 233 | 2,3,11,12,20,21,29,30-Octa(4-t-butoxybutylthio)-NcAlOH |
| 234 | 2,3,11,12,20,21,29,30-Octamethyl-NcAlOH |
| 235 | 2,3,11,12,20,21,29,30-Octa-(4-t-butylphenylthio)-Nc—Si(OH)$_2$ |
| 236 | 2(3), 11(12), 20(21), 29(30)-Tetradiethylamino-NcAlOH |
| 237 | 2(3), 11(12), 20(21), 29(30)-Tetramorpholino-NcAlOCOCF$_3$ |
| 238 | 2(3), 11(12), 20(21), 29(30)-Tetra-O(C$_2$H$_4$O)$_2$CH$_3$—Nc—SiCl$_2$ |
| 239 | 2(3), 11(12), 20(21), 29(30)-Tetra-O(C$_2$H$_4$O)$_3$CH$_3$—Nc—Si(OH)$_2$ |
| 240 | 2(3), 11(12), 20(21), 29(30)-Tetra[(CH$_3$)$_3$—Si—CH$_2$S]—Nc—Si[OSi(C$_4$H$_9$)$_3$]$_2$ |
| 241 | 2(3), 11(12), 20(21), 29(30)-Tetra[(C$_2$H$_5$)$_3$—Si—(CH$_2$)$_2$S]—Nc—Si[OSi(CH$_3$)$_3$]$_2$ |
| 242 | 2(3), 11(12), 20(21), 29(30)-Tetra[(C$_6$H$_{11}$)$_3$—Si—CH$_2$—S]—Nc—Si[OSi(OCH$_3$)$_3$]$_2$ |
| 243 | 2(3), 11(12), 20(21), 29(30)-Tetra[(CH$_3$O)$_3$—Si—(CH$_2$)$_3$—S]—Nc—Ge[OSi(C$_2$H$_5$)$_3$]$_2$ |
| 244 | 2(3), 11(12), 20(21), 29(30)-Tetra[(C$_6$H$_5$O)$_3$—Si—CH$_2$—S]—Nc—Ge[OSi(OCH$_3$)$_3$]$_2$ |
| 245 | 2(3), 11(12), 20(21), 29(30)-Tetra[(CH$_3$)$_3$—Si—CH$_2$CH$_2$—O]—Nc—Si(OH)$_2$] |
| 246 | 2(3), 11(12), 20(21), 29(30)-Tetra[(CH$_3$)$_3$—SiC(Cl)$_2$CH$_2$S]—Nc—Si[OSi(CH$_3$)$_3$]$_2$ |
| 247 | 2(3), 11(12), 20(21), 29(30)-Tetra[(C$_6$H$_5$)$_3$—Si—CH$_2$O]—Nc—AlOH |
| 248 | 2(3), 11(12), 20(21), 29(30)-Tetra[(CH$_3$)$_3$—Si—CH$_2$S]—Nc—Si[OSi(C$_2$H$_5$)$_3$]$_2$ |
| 249 | 2(3), 11(12), 20(21), 29(30)-Tetra[(CH$_3$)$_3$—Si—CH$_2$S]—Nc—Si[OC$_{18}$H$_{37}$]$_2$ |
| 250 | 2(3), 11(12), 20(21), 29(30)-Tetra[(CH$_3$)$_2$C$_6$H$_5$Si—(CH$_2$)$_4$O]—Nc—AlOH |
| 251 | 2,3,11,12,20,21,29,30-Octa[(CH$_3$)$_3$Si—CH$_2$S]—Nc—Si(OH)$_2$ |
| 252 | 5(36), 9(14), 18(23), 27(32)-Tetra(4-t-butylphenyl)-2(3),11(12),20(21), 29(30)-tetra-t-butyl-NcH$_2$ |
| 253 | 5(36), 9(14), 18(23), 27(32)-Tetra(4-hexylphenyl)-NcH$_2$ |
| 254 | 5(36), 9(14), 18(23), 27(32)-Tetra(4-octylphenyl)-NcH$_2$ |
| 255 | 5(36), 9(14), 18(23), 27(32)-Tetra(4-dodecylohexyl)-NcAlOH |
| 256 | 1(4), 10(13), 19(22), 28(31)-Tetra(dodecylamino)-NcAlCl |
| 257 | 1(4), 10(13), 19(22), 28(31)-Tetra(n-octylamino)-NcAlOH |
| 258 | 1(4), 10(13), 19(22), 28(31)-Tetra(n-octylamino)-NcAlOC$_6$H$_3$-3,5-di-CO$_2$CH$_3$ |
| 259 | 2(3), 11(12), 20(21), 29(30)-Tetra(dodecylthio)-NcAlOH |
| 260 | 2(3), 11(12), 20(21), 29(30)-Tetra(n-octylthio)-NcAlCl |
| 261 | 2(3), 11(12), 20(21), 29(30)-Tetra(dodecylthio)-NcAlOC$_6$H$_3$-3,5-di-CO$_2$CH$_3$ |
| 262 | 2,3,11,12,20,21,29,30-Octa(dodecylthio)NcSi(OH)$_2$ |
| 263 | 2,3,11,12,20,21,29,30-Octa(dodecylthio)NcSi(OC$_6$H$_4$-4-CO$_2$CH$_3$)$_2$ |
| 264 | NcSi(OCOC$_6$H$_4$-4-t-butyl)$_2$ |
| 265 | NcSi(OCOC$_6$H$_4$-4-CO$_2$(CH$_2$)$_{12}$CH$_3$]$_2$ |
| 266 | NcSi[COCONHC$_6$H$_4$-4-CO$_2$(CH$_2$CH$_2$O)$_3$CH$_3$]$_2$ |
| 267 | NcSi[OCONHC$_6$H$_3$-3,5-di-CO$_2$CH$_2$CH(C$_2$H$_5$)C$_4$H$_9$-n]$_2$ |
| 268 | 2(3), 11(12), 20(21), 29(30)-Tetra-t-butyl-NcMg |
| 269 | NcSi[OC$_6$H$_3$-3,5-diCO$_2$CH$_2$CH(C$_2$H$_5$)C$_4$H$_9$-n]$_2$ |
| 270 | NcAlOC$_6$H$_4$-4-OC$_{10}$H$_{21}$ |
| 271 | 2(3), 11(12), 20(21), 29(30)-Tetra(2-ethylhexylamino)NcH$_2$ |
| 272 | 2(3), 11(12), 20(21), 29(30)-Tetra(4-t-butylphenoxy)NcZn |
| 273 | 2(3), 11(12), 20(21), 29(30)-Tetra(4-n-hexylphenylthio)NcMg |
| 274 | 2(3), 11(12), 20(21), 29(30)-Tetra[4-CH=N—CH$_2$(C$_2$H$_5$)C$_4$H$_9$n-phenoxy]NcH$_2$ |
| 275 | NcSi[OC$_6$H$_4$-4-CH=N—C$_6$H$_4$-4-CO$_2$CH$_2$CH(C$_2$H$_5$)C$_4$H$_9$-n]$_2$ |

TABLE 5

CROCONIC ACID DERIVED COMPOUNDS

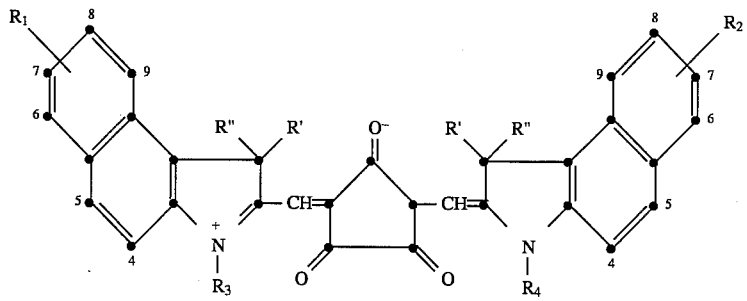

| EX. NO. | $R_1, R_2$ | $R_3, R_4$ | R', R" |
|---|---|---|---|
| 276 | 7-$CO_2(CH_2)_3CH_3$ | H | $CH_3$ |
| 277 | 7-$CO_2CH_2CH(C_2H_5)(CH_2)_3CH_3$ | H | $CH_3$ |
| 278 | 7-$CO_2NHC_8H_{17}$ | H | $CH_3$ |
| 279 | 7-$CO_2NHC_6H_4$-4-$C(CH_3)_3$ | $CH_3$ | $CH_3$ |
| 280 | 7-$SO_2NHC_{12}H_{25}$ | $C_6H_5$ | $CH_3$ |
| 281 | 7-$(CH_2)_7CH_3$ | $CH_2CH_3$ | $CH_3$ |
| 282 | 7-$CO_2C_6H_{10}$-4-$CH_3$ | $CH_3$ | $CH_3, CH_2CH_3$ |
| 283 | 7-$SO_2(CH_2)_3CH(CH_3)CH_3$ | H | $CH_3, CH(CH_3)_2$ |
| 284 | 7-$CO_2C_6H_4$-4-$O(CH_2)_{12}CH_3$ | H | $CH_3, CH_2CH(CH_3)_2$ |
| 285 | 7-$CO_2NHC_6H_4$-4-$C_6H_{11}$ | H | $CH_3$ |
| 286 | 7-$SO_2NHCH_2(CH_2CH_3)C_6H_9$—n | H | $CH_3$ |
| 287 | 7-$SO_2N(C_4H_9$—n$)C_6H_{11}$ | H | $CH_3$ |
| 288 | 7-$S(CH_2)_{10}CH_3$ | H | $CH_3$ |
| 289 | 7-$OCH_2CH(C_2H_5)C_4H_9$—n | H | $CH_3$ |
| 290 | 8-$(CH_2)_3CH_3$ | H | $CH_3$ |

We claim:

1. A method for tagging a petroleum hydrocarbon for identification purposes, which comprises dissolving at ambient temperature in said hydrocarbon a near infrared fluorophoric compound selected from the group consisting of squaraines phthalocyanines and naphthalocyanines having at least one straight or branched chain $C_4$ to $C_{20}$ alkyl group, and croconic acid derivatives.

2. The method of claim 1, wherein the petroleum hydrocarbon is gasoline.

3. The method of claim 1, wherein the petroleum hydrocarbon is kerosene.

4. The method of claim 1, wherein the petroleum hydrocarbon is lubricant oil.

5. The method of claim 1, wherein the petroleum hydrocarbon is furnace oil.

6. The method of claim 1, wherein the near infrared fluorophoric compound is selected from the group consisting of phthalocyanines, 2,3-naphthalocyanines, squaraines and croconic acid derivatives and correspond to Formulae I, II, III, and IV, respectively:

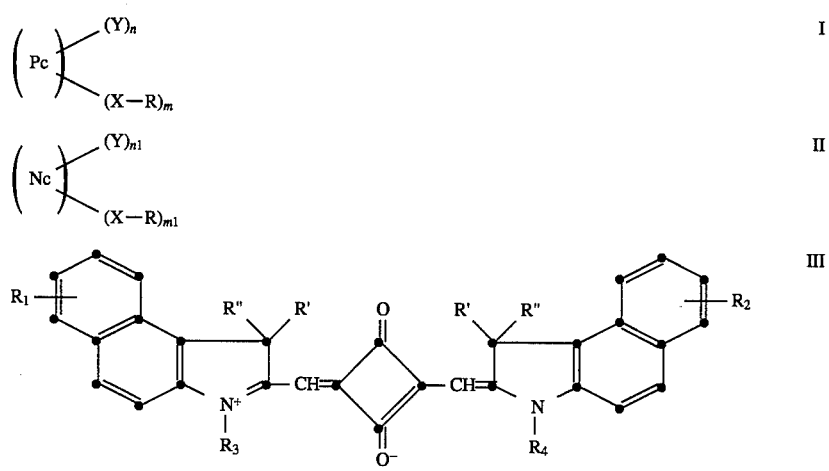

-continued

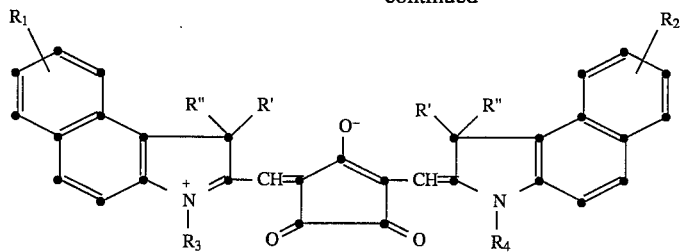

wherein Pc and Nc represent the phthalocyanine and naphthalocyanine moieties of Formulae Ia and IIa,

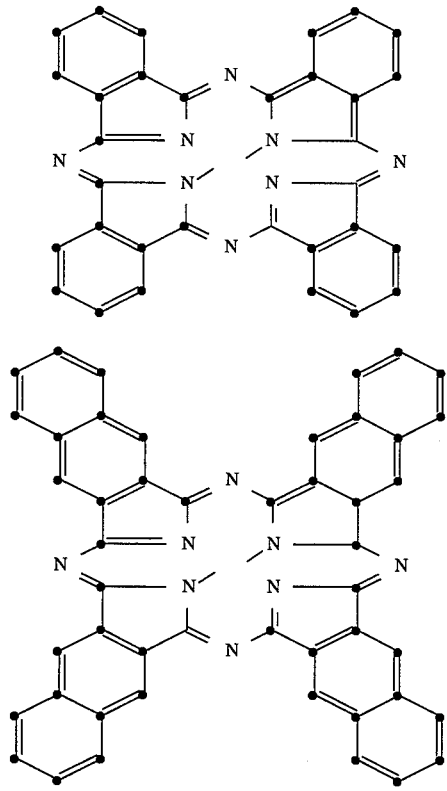

respectively, covalently bonded to hydrogen or to halometals, organometallic groups, and oxymetals selected from the group consisting of $AlCl$, $AlBr$, $AlF$, $AlOR_5$, $AlSR_5$, $SiCl_2$, $SiF_2$, $Si(OR_6)_2$, $Si(SR_6)_2$, $Zn$ and $Mg$, wherein $R_5$ and $R_6$ are selected from hydrogen, alkyl, aryl, heteroaryl, alkanoyl, arylcarbonyl, arylaminocarbonyl, trifluoroacetyl, $$-(CH_2CH_2O)_zR, \quad -(CH_2CHO)_zR,$$
$$\qquad\qquad\qquad\qquad\qquad |$$
$$\qquad\qquad\qquad\qquad\qquad CH_3$$

groups of the formulae

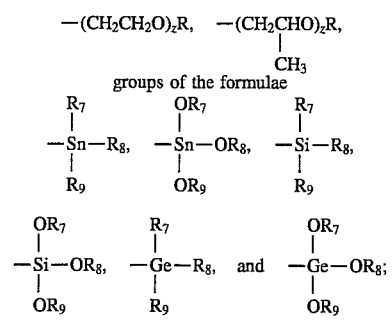

wherein $R_7$, $R_8$ and $R_9$ are independently selected from alkyl, phenyl or phenyl substituted with alkyl, alkoxy or halogen;

X is selected from oxygen, sulfur, selenium, tellurium or a group of the formula $N-R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, aryl, heteroaryl, halogen or hydrogen;

R is selected from hydrogen, unsubstituted or substituted alkyl, alkenyl, alkynyl, $C_3$–$C_8$ cycloalkyl, aryl, heteroaryl, alkylene

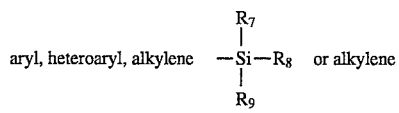

or alkylene

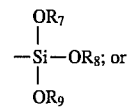

—$(X-R)_m$ is one or more groups selected from alkylsulfonylamino, arylsulfonylamino, or a group selected from the formulae —$X(C_2H_4O)_zR$,

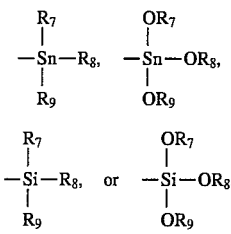

wherein R is as defined above; Z is an integer of from 1–4; or two —$(X-R)_m$ groups can be taken together to form divalent substituents of the formula

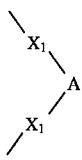

wherein each $X_1$ is independently selected from —O—, —S—, or —N—$R_{10}$ and A is selected from ethylene; propylene; trimethylene; and such groups substituted with lower alkyl, lower alkoxy, aryl and cycloalkyl; 1,2-phenylene and 1,2-phenylene containing 1–3 substituents selected from lower aklyl, lower alkoxy or halogen; R' and R" are independently selected from lower alkyl and cycloalkyl; $R_1$ and $R_2$ are independently selected from hydrogen, alkyl, alkoxy, halogen, aryloxy, alkylthio, arylthio, alkylsulfonyl, arylsulfonyl, alkyl-sulfonylamino, arylsulfonylamino, cycloalkyl-sulfonylamino, unsubstituted and substituted carbamoyl and sulfamyl, alkoxycarbonyl, cycloalkoxycarbonyl, alkanoyloxy,

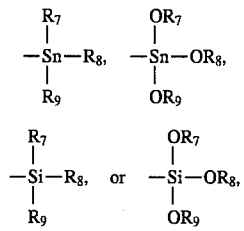

$R_3$ and $R_4$ are independently selected from hydrogen, lower alkyl, alkenyl or aryl; n is an integer from 0–16; $n_1$ is an integer from 0–24, m is an integer from 0–16; and $m_1$ is an integer from 0–24; provided that the sums of n+m and $n_1+m_1$ are 16 and 24, respectively.

7. The method of claim 6, wherein the near infrared fluorescing compound is a squaraine compound of Formula III, and wherein $R_1$ and $R_2$ are independently alkoxycarbonyl.

8. The method of claim 6, wherein the near infrared fluorescing compound is a 2,3-naphthalocyanine compound of Formula II, and wherein the naphthalocyanine moiety is bonded to hydrogen, AlCl, AlOH, AlOR$_5$, SICl$_2$, Si(OH)$_2$, Si(OR$_6$)$_2$, Zn or Mg, $m_1$ is 0, Y is alkyl and $n_1$ is 24 and wherein the Y groups represent at least four alkyl or aryl groups.

9. The method of claim 6, wherein the naphthalocyanine compound of Formula II is bonded to hydrogen.

10. The method of claim 6, wherein the near infrared fluorescing compound is a phthalocyanine compound of Formula I, and wherein X is oxygen, R is aryl or alkyl, Y is hydrogen, m is 4, and n is 12; and wherein the phthalocyanine moiety is bonded to hydrogen, AlCl, AlOH, AlO-COCF$_3$, AlOR$_5$, SICl$_2$, Si(OH)$_2$, Si(OR$_6$)$_2$, Zn or Mg.

11. The method of claim 6, wherein the phthalocyanine compound of Formula I is bonded to hydrogen.

12. A method for identifying a petroleum hydrocarbon, wherein said product has one or more near infrared fluorophoric compounds dissolved therein, which comprises the steps:
  (a) exposure of a petroleum hydrocarbon composition to electromagnetic radiation having wavelengths of 670–850 nm, wherein said petroleum hydrocarbon composition comprises a petroleum hydrocarbon material having dissolved therein one or more near infrared fluorescent tagging compounds selected from the group consisting of squaraines, phthalocyanines and naphthalocyanines having at least one straight or branched chain $C_4$ to $C_{20}$ alkyl group and croconic acid derivatives, wherein said tagging compound(s) is (are) present in a concentration sufficient to impart detectable fluorescence when exposed to electromagnetic radiation of about 670–850 nm provided by light sources; followed by
  (b) detection of the emitted fluorescent radiation by near infrared detection means.

13. The method of claim 12, wherein the petroleum hydrocarbon material is gasoline.

14. The method of claim 12, wherein the petroleum hydrocarbon material is kerosene.

15. The method of claim 12, wherein the petroleum hydrocarbon material is lubricant oil.

16. The method of claim 12, wherein the petroleum hydrocarbon material is furnace oil.

17. The method of claim 12, wherein the near infrared fluorophoric compound is selected from the group consisting of phthalocyanines, 2,3-naphthalocyanines, squaraines and croconic acid derivatives and correspond to Formulae I, II, III, and IV, respectively:

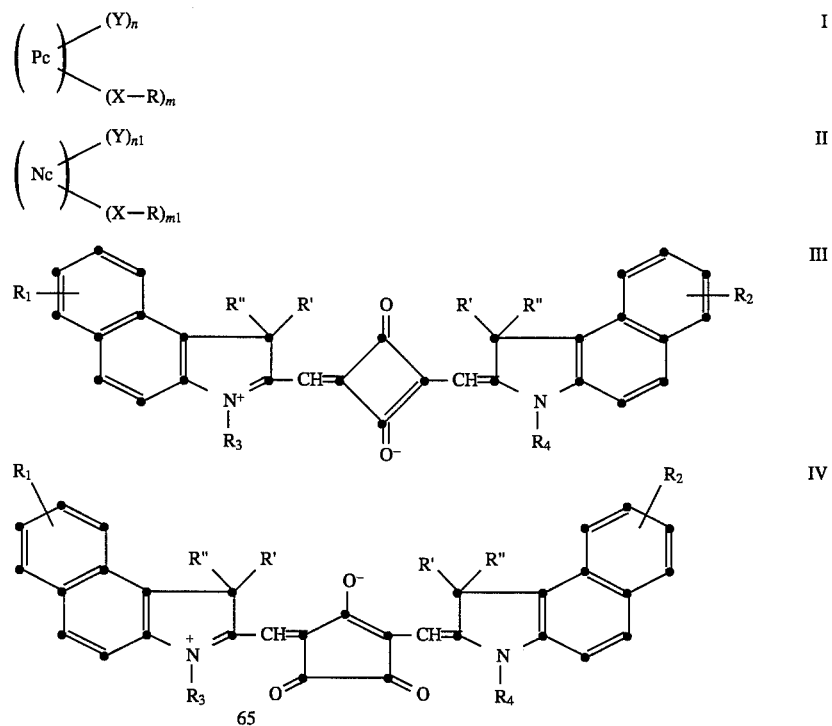

wherein Pc and Nc represent the phthalocyanine and naphthalocyanine moieties of Formulae Ia and IIa,

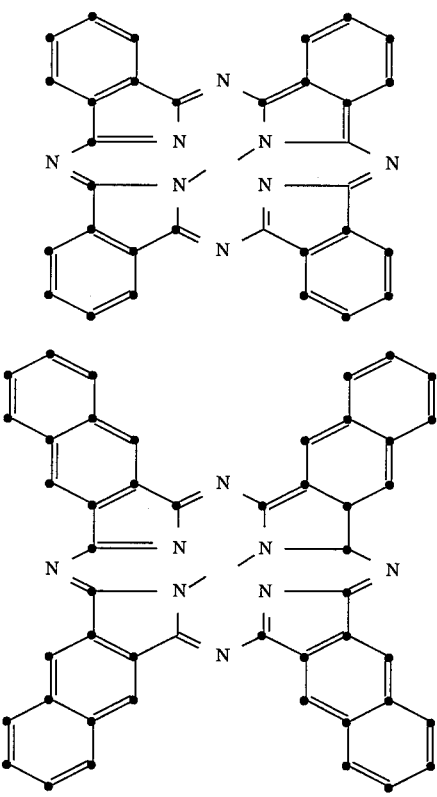

Ia

IIa respectively, covalently bonded to hydrogen or to halometals, organometallic groups, and oxymetals selected from the group consisting of AlCl, AlBr, AlF, $AlOR_5$, $AlSR_5$, $SiCl_2$, $SiF_2$, $Si(OR_6)_2$, $Si(SR_6)_2$, Zn and Mg, wherein $R_5$ and $R_6$ are selected from hydrogen, alkyl, aryl, heteroaryl, alkanoyl, arylcarbonyl, arylaminocarbonyl, trifluoroacetyl,

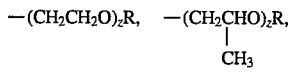

groups of the formulae

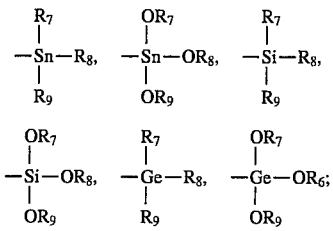

wherein $R_7$, $R_8$ and $R_9$ are independently selected from alkyl, phenyl or phenyl substituted with alkyl, alkoxy or halogen;

X is selected from oxygen, sulfur, selenium, tellurium or a group of the formula $N–R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, aryl, heteroaryl, halogen or hydrogen;

R is selected from hydrogen, unsubstituted or substituted alkyl, alkenyl, alkynyl, $C_3–C_8$ cycloalkyl, aryl, heteroaryl, alkylene

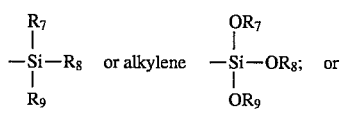

—(X-R)$_m$ is one or more groups selected from alkylsulfonylamino, arylsulfonylamino, or a group selected from the formulae —$X(C_2H_4O)_zR$,

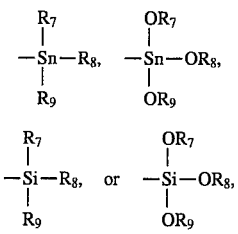

wherein R is as defined above; Z is an integer of from 1–4; or two —(X-R)$_m$ groups can be taken together to form divalent substituents of the formula

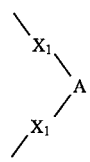

wherein each $X_1$ is independently selected from —O—, —S—, or —N–$R_{10}$ and A is selected from ethylene; propylene; trimethylene; and such groups substituted with lower alkyl, lower alkoxy, aryl and cycloalkyl; 1,2-phenylene and 1,2-phenylene containing 1–3 substituents selected from lower aklyl, lower alkoxy or halogen; R' and R" are independently selected from lower alkyl and cycloalkyl; $R_1$ and $R_2$ are independently selected from hydrogen, alkyl, alkoxy, halogen, aryloxy, alkylthio, arylthio, alkylsulfonyl, arylsulfonyl, alkyl-sulfonylamino, arylsulfonylamino, cycloalkylsulfonylamino, unsubstituted and substituted carbamoyl and sulfamyl, alkoxycarbonyl, cycloalkoxycarbonyl, alkanoyloxy,

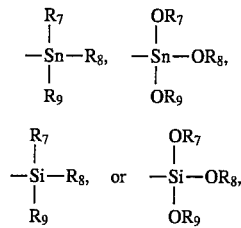

$R_3$ and $R_4$ are independently selected from hydrogen, lower alkyl, alkenyl or aryl; n is an integer from 0–16; $n_1$ is an integer from 0–24, m is an integer from 0–16; $m_1$ is an integer from 0–24; provided that the sums of n+m and $n_1+m_1$ are 16 and 24, respectively.

18. The method of claim 17, wherein the near infrared fluorescing compound is a squaraine compound of Formula III, and wherein $R_1$ and $R_2$ are independently alkoxycarbonyl.

19. The method of claim 17, wherein the near infrared fluorescing compound is a 2,3-naphthalocyanine compound of Formula II, and wherein the naphthalocyanine moiety is bonded to hydrogen, AlCl, AlOH, AlOR$_5$, SiCl$_2$, Si(OH)$_2$, Si(OR$_6$)$_2$, Zn or Mg, m$_1$ is 0, Y is alkyl and n$_1$ is 24 and wherein the Y groups represent at least four alkyl or aryl groups.

20. The method of claim 17, wherein the naphthalocyanine compound of Formula II is bonded to hydrogen.

21. The method of claim 17, wherein the near infrared fluorescing compound is a phthalocyanine compound of Formula I, and wherein X is oxygen, R is aryl or alkyl, Y is hydrogen, m is 4, and n is 12; and wherein the phthalocyanine moiety is bonded to hydrogen, AlCl, AlOH, AlO-COCF$_3$, AlOR$_5$, SiCl$_2$, Si(OH)$_2$, Si(OR$_6$)$_2$, Zn or Mg.

22. The method of claim 17, wherein the phthalocyanine compound of Formula I is bonded to hydrogen.

23. A petroleum hydrocarbon having dissolved therein at least one near infrared fluorophoric compound selected from the group consisting of squaraines, phthalocyanines and naphthalocyanines having at least one straight or branched chain C$_4$ to C$_{20}$ alkyl group, and croconic acid derivatives.

24. The petroleum hydrocarbon of claim 23, wherein the near infrared fluorophoric compound is selected from the group consisting of phthalocyanines, 2,3-naphthalocyanines squaraines (squaric acid derivatives) and croconic acid derivatives and correspond to Formulae I, II, III, and IV, respectively:

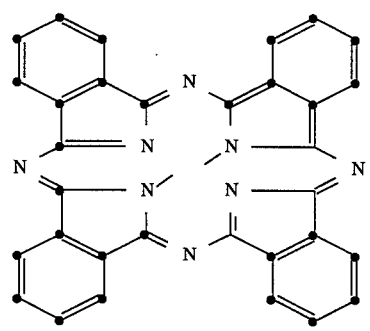

Ia

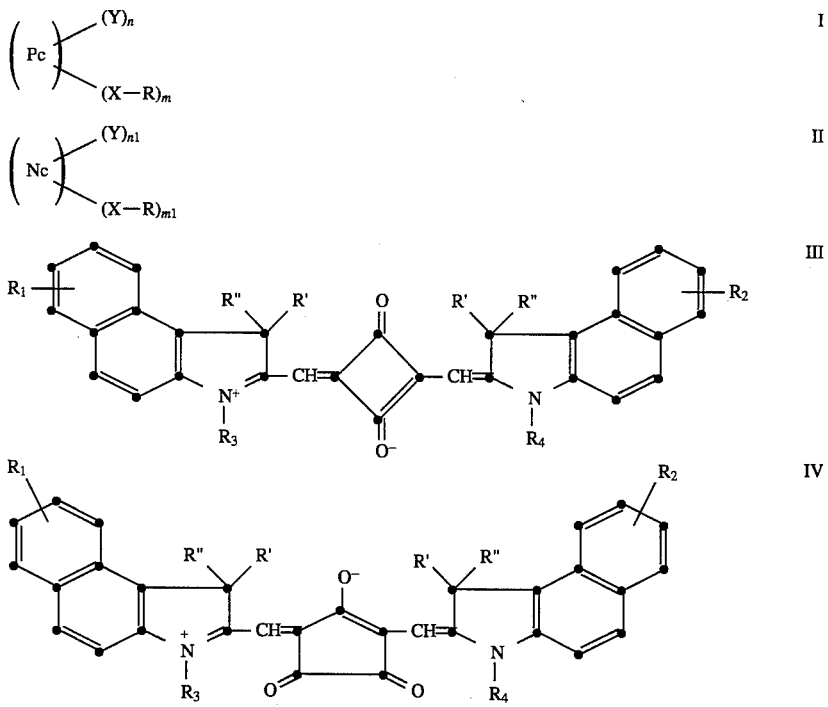

I

II

III

IV wherein Pc and Nc represent the phthalocyanine and naphthalocyanine moieties of Formulae Ia and IIa,

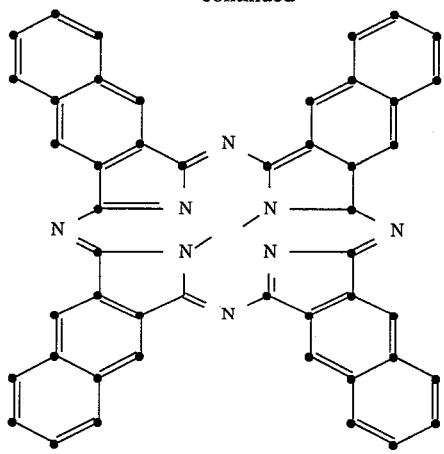

respectively, covalently bonded to hydrogen or to halometals, organometallic groups, and oxymetals selected from the group consisting of AlCl, AlBr, AlF, $AlOR_5$, $AlSR_5$, $SiCl_2$, $SiF_2$, $Si(OR_6)_2$, $Si(SR_6)_2$, Zn and Mg, wherein $R_5$ and $R_6$ are selected from hydrogen, alkyl, aryl, heteroaryl, alkanoyl, arylcarbonyl, arylaminocarbonyl, trifluoroacetyl,

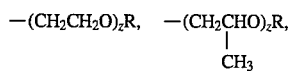

groups of the formulae

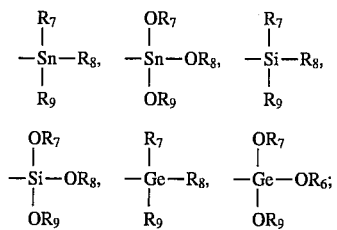

wherein $R_7$, $R_8$ and $R_9$ are independently selected from alkyl, phenyl or phenyl substituted with alkyl, alkoxy or halogen;

X is selected from oxygen, sulfur, selenium, tellurium or a group of the formula $N-R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, aryl, heteroaryl, halogen or hydrogen;

R is selected from hydrogen, unsubstituted or substituted alkyl, alkenyl, alkynyl, $C_3-C_8$ cycloalkyl, aryl, heteroaryl, alkylene

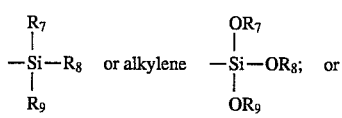

—(X–R)$_m$ is one or more groups selected from alkylsulfonylamino, arylsulfonylamino, or a group selected from the formulae —X(C$_2$H$_4$O)$_z$R,

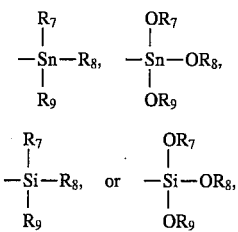

wherein R is as defined above; Z is an integer of from 1–4; or two —(X–R)$_m$ groups can be taken together to form divalent substituents of the formula

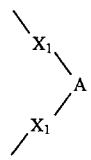

wherein each $X_1$ is independently selected from —O—, —S—, or —N–$R_{10}$ and A is selected from ethylene; propylene; trimethylene; and such groups substituted with lower alkyl, lower alkoxy, aryl and cycloalkyl; 1,2-phenylene and 1,2-phenylene containing 1–3 substituents selected from lower aklyl, lower alkoxy or halogen; R' and R" are independently selected from lower alkyl and cycloalkyl; $R_1$ and $R_2$ are independently selected from hydrogen, alkyl, alkoxy, halogen, aryloxy, alkylthio, arylthio, alkylsulfonyl, arylsulfonyl, alkylsulfonylamino, arylsulfonylamino, cycloalkylsulfonylamino, unsubstituted and substituted carbamoyl and sulfamyl, alkoxycarbonyl, cycloalkoxycarbonyl, alkanoyloxy, $R_3$ and $R_4$ are independently selected from hydrogen, lower alkyl, alkenyl or aryl; n is an integer from 0–16; $n_1$ is an integer from 0–24, m is an integer from 0–16; $m_1$ is an integer from 0–24; provided that the sums of n+m and $n_1$+$m_1$ are 16 and 24, respectively.

25. The petroleum hydrocarbon of claim 23, wherein the near infrared fluorescing compound is a squaraine compound of Formula III, and wherein $R_1$ and $R_2$ are independently alkoxycarbonyl.

26. The petroleum hydrocarbon of claim 23, wherein the near infrared fluorescing compound is a 2,3-naphthalocyanine compound of Formula II, and wherein the naphthalocyanine moiety is bonded to hydrogen, AlCl, AlOH, $AlOR_5$, $SiCl_2$, $Si(OH)_2$, $Si(OR_6)_2$, Zn or Mg, $m_1$ is 0, Y is alkyl and $n_1$ is 24 and wherein the Y groups represent at least four alkyl or aryl groups.

27. The petroleum hydrocarbon of claim 24, wherein the naphthalocyanine compound of Formula II is bonded to hydrogen.

28. The petroleum hydrocarbon of claim 24, wherein the near infrared fluorescing compound is a phthalocyanine compound of Formula I, and wherein X is oxygen, R is aryl or alkyl, Y is hydrogen, m is 4, and n is 12; and wherein the phthalocyanine moiety is bonded to hydrogen, AlCl, AlOH, $AlOCOCF_3$, $AlOR_5$, $SiCl_2$, $Si(OH)_2$, $Si(OR_6)_2$, Zn or Mg.

29. The petroleum hydrocarbon of claim 24, wherein the phthalocyanine compound of Formula I is bonded to hydrogen.

30. The petroleum hydrocarbon of claim 24, wherein the near infrared fluorescing compound is selected from the group consisting of 1(4) , 8(11) , 15(18) , 22(25)-tetra[4(2- ethylhexyloxycarbonyl)phenylthio]PcH$_2$; 2(3), 9(10), 16(17), 23(24)-Tetra-(4-nonylphenoxy)PcH$_2$; 2(3), 9(10), 16(17), 23(24)-Tetra-(4-isoamylphenylthio)-PcZn; 2(3), 9(10), 16(17), 23(24)-tetra(2-ethylhexylamino)PcH$_2$; 2(3), 9(10), 16(17), 23(24)-tetra(3,5-di-t-butylphenoxy)PcH$_2$; 2(3), 9(10), 16(17), 23(24)-tetra[4-(carbo-2-ethylhexyloxy)phenoxy]PcH$_2$; 2(3), 9(10), 16(17), 23(24)-tetra (3-pentadecylphenoxy)-PcH$_2$; 2(3), 11(12), 20(21), 29(30)-tetra-t-butyl-NcH$_2$; 2(3), 11(12), 20(21), 29(30)-tetraactyl-NcH$_2$; and 2(3), 11(12), 20(21), 29(30)-tetra-t-butyl-NcZn; 1, 4, 8, 11, 15, 18, 22, 25-octabutoxy-PcH$_2$; 2(3), 9(10), 16(17), 23(24)-tetra(phenylthio)pcH$_2$; 2(3), 9(10), 16(17), 23(24)-tetra(4-t-butylphenylthio)pcH$_2$; 5, 9, 14, 18, 23, 27, 32, 36-octabutoxy-NcH$_2$; 5(36), 14(9), 23(18), 32(27)-tetra(4-t-butylphenyl)-3(2), 12(11), 21(20), 30(29)-tetra-t-butyl-NcH$_2$; 5(36), 14(9), 23(18), 32(27)-tetra-[4-(2-ethylhexylamino)phenyl]-3(2), 12(11), 21(20), 30(29)-tetra-(2-ethylhexylamino)NcH$_2$; wherein Pc is a phthalocyanine moiety and Nc is a naphthalocyanine moiety.

31. The petroleum hydrocarbon of claim 24 wherein the near infrared fluorescing compound is 2(3), 11(12), 20(21), 29(30)-tetra-t-butyl-NcH$_2$, wherein Nc is a naphthalocyanine moiety.

32. The petroleum hydrocarbon of claim 23, wherein the near infrared flurophoric compound is non-metallated.

\* \* \* \* \*

US005525516B1

REEXAMINATION CERTIFICATE (3927th)

United States Patent [19]
Krutak et al.

[11] B1 5,525,516
[45] Certificate Issued Nov. 9, 1999

[54] METHOD FOR TAGGING PETROLEUM PRODUCTS

[75] Inventors: James J. Krutak; Michael R. Cushman; Max A. Weaver, all of Kingsport, Tenn.

[73] Assignee: Eastman Chemical Company, Kingsport, Tenn.

Reexamination Request:
No. 90/004,997, Jun. 1, 1998

Reexamination Certificate for:
| | |
|---|---|
| Patent No.: | 5,525,516 |
| Issued: | Jun. 11, 1996 |
| Appl. No.: | 08/315,386 |
| Filed: | Sep. 30, 1994 |

[51] Int. Cl.⁶ .................................................. G01N 21/64
[52] U.S. Cl. ................................ 436/56; 436/27; 436/29; 436/172
[58] Field of Search ................................ 436/27, 29, 56, 436/172

[56] References Cited

U.S. PATENT DOCUMENTS

| | | | |
|---|---|---|---|
| 3,733,178 | 5/1973 | Eriksen ................................... | 23/230 B |
| 3,806,727 | 4/1974 | Leonard et al. ......................... | 250/301 |
| 3,964,294 | 6/1976 | Shair et al. .................................. | 73/53 |
| 4,141,692 | 2/1979 | Keller et al. ................................ | 44/59 |
| 4,146,604 | 3/1979 | Kleinerman ................................ | 424/3 |
| 4,301,372 | 11/1981 | Giering et al. ............................. | 424/3 |
| 4,398,505 | 8/1983 | Cahill ..................................... | 123/1 A |
| 4,435,301 | 3/1984 | Brannen et al. ........................ | 252/33.2 |
| 4,606,859 | 8/1986 | Duggan et al. .......................... | 540/122 |
| 4,622,179 | 11/1986 | Eda .......................................... | 60/732 |
| 4,666,672 | 5/1987 | Miller et al. .............................. | 422/68 |
| 4,783,314 | 11/1988 | Hoot et al. ................................. | 422/3 |
| 4,904,567 | 2/1990 | Maeda et al. ........................... | 430/270 |
| 4,978,625 | 12/1990 | Wagner et al. .......................... | 436/518 |
| 5,034,613 | 7/1991 | Denk et al. ........................... | 250/458.1 |
| 5,230,781 | 7/1993 | Middendorf et al. ................. | 204/182.8 |
| 5,254,625 | 10/1993 | Weaver et al. .......................... | 525/165 |
| 5,302,740 | 4/1994 | Krutak et al. ............................ | 558/401 |
| 5,331,140 | 7/1994 | Stephany ................................ | 235/462 |
| 5,710,046 | 1/1998 | Rutledge et al. .......................... | 436/56 |
| 5,723,338 | 3/1998 | Rutledge et al. .......................... | 436/56 |
| 5,804,447 | 9/1998 | Alberti et al. ............................. | 436/56 |

FOREIGN PATENT DOCUMENTS

| | | |
|---|---|---|
| 9361310 | 4/1931 | United Kingdom . |
| WO92/08676 | 5/1992 | WIPO . |
| WO94/02570 | 2/1994 | WIPO . |
| WO94/04918 | 3/1994 | WIPO . |
| WO94/12874 | 6/1994 | WIPO . |

OTHER PUBLICATIONS

Kwong–Yung Chu And John Griffiths*, J.Chem. Research (S), 1978, pp. 180–181.

James R. Darwent, Ian Mccubbin And D. Phillips, Davy Faraday Research Laboratory, J. Chem. Soc., Faraday Trans. 1982, 78, pp. 347–357.

Totaro Imasaka, Akinori Yoshitake, And Nobuhiko Ishibashi, Anal. Chem. 1984,56. pp. 1077–1079.

Bob L. Wheeler, G. Nagasubramanian, Allen J. Bard, Lee A. Schechtman, David R. Dininny, And Malcolm E. Kenney, J. Am. Chem. Soc. 1984, 106, pp. 7404–7410.

J.D. Winefordner and M. Rutledge, Applied Spectroscopy, vol. 39, No. 3, 1985, pp. 377–391.

Kouji Sauda, Totaro Imasaka, And Nobuhiko Ishibashi, Anal. Chem. 1986, 58. pp. 2649–2653.

B.W. Smith, M.J. Rutledge and J.D. Winefordner, Applied Spectroscopy, vol. 41, No. 4, 1987, pp. 613–620.

Hiroyuki Nakazumi and Masaru Matsuoka, Chem. Rev. 1992, 92. pp. 1197–1226.

Steven A. soper and Quincy L. Mattingly, J. Am. Chem. Soc. 1994, 116. pp. 3744–3752.

James R. Heath and Richard J. Saykally, Spectroscopy, pp. 7–21.

H.J. Hwang, A. Van Orden, K. Tanaka, E.W. Kuo, J.R. Heath, and R.J. Saykally, Molecular Physics, 1993, vol. 79, No. 4, pp. 769–776.

American Petroleum Institue, Conf. on Prevention and Control of Oil Pollution, Mar. 25–27, 1975, pp. 87–91.

James H. Brannon and Douglas Magde, Journal of the American Chemical Society, 102:1, Jan. 2, 1980, pp. 62–65.

Environmental and Applied Sciences Center, Research Division, "Oil Tagging System Study", May 1970.

James McVie, Roy S. Sinclair and T. George Truscott, Chemistry Department, Paisley College, Paisley, Scotland, "Triplet States of Copper and Metal–free Phthalocyanines", Mar. 1978.

G. Ferraudi and S. Muralidharan, "Photochemistry of Transition–Metal Phthalocyanines. Analysis of the Photochemical and Photophysical Properties of the Acido(phthalocyaninato)rhodium(III) Complexes", Inorg. Chem., 1983, 22, 1369–1374.

*Primary Examiner*—Randy Gulakowski

[57] ABSTRACT

This invention provides a method for imparting invisible markings for identification purposes to petroleum hydrocarbons by incorporating one or more infrared fluorescing compounds therein. Certain infrared fluorophores from the classes of squaraines (derived from squaric acid), phthalocyanines and naththalocyanines are useful in providing invisibly marked petroleum hydrocarbons such as crude oil, lubricating oils, waxes, gas oil (furnace oil), diesel oil, kerosene and in particular gasoline. The near infrared fluorophores are added to the hydrocarbons at extremely low levels and are detected by exposing the marked hydrocarbon compositions to near infrared radiation having a wavelength in the 670–850 nm range and then detecting the emitted fluorescent light via near infrared light detection means.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–32 is confirmed.

* * * * *